US009549691B2

(12) United States Patent
Tran

(10) Patent No.: US 9,549,691 B2
(45) Date of Patent: *Jan. 24, 2017

(54) WIRELESS MONITORING

(71) Applicant: Bao Tran, Saratoga, CA (US)

(72) Inventor: Bao Tran, Saratoga, CA (US)

(*) Notice: Subject to any disclaimer, the term of this patent is extended or adjusted under 35 U.S.C. 154(b) by 13 days.

This patent is subject to a terminal disclaimer.

(21) Appl. No.: 14/260,228

(22) Filed: Apr. 23, 2014

(65) Prior Publication Data

US 2014/0235965 A1    Aug. 21, 2014

Related U.S. Application Data

(63) Continuation of application No. 11/832,735, filed on Aug. 2, 2007, now Pat. No. 8,750,971, and a
(Continued)

(51) Int. Cl.
| | |
|---|---|
| *A61B 5/02* | (2006.01) |
| *A61B 5/024* | (2006.01) |
| *A61B 5/11* | (2006.01) |
| *A61B 5/00* | (2006.01) |
| *A61B 5/0205* | (2006.01) |

(Continued)

(52) U.S. Cl.
CPC ............ *A61B 5/1128* (2013.01); *A61B 5/002* (2013.01); *A61B 5/0006* (2013.01); *A61B 5/0059* (2013.01); *A61B 5/024* (2013.01); *A61B 5/0205* (2013.01); *A61B 5/026* (2013.01); *A61B 5/02028* (2013.01); *A61B 5/02042* (2013.01); *A61B 5/0402* (2013.01); *A61B 5/04005* (2013.01); *A61B 5/0476* (2013.01); *A61B 5/0488* (2013.01); *A61B 5/1075* (2013.01); *A61B 5/113* (2013.01); *A61B 5/1113* (2013.01); *A61B 5/1117* (2013.01); *A61B 5/1118* (2013.01); *A61B 5/447* (2013.01); *A61B 5/4875* (2013.01); *A61B 5/4881* (2013.01); *A61B 5/7264* (2013.01); *A61B 5/7267* (2013.01); *A61B 5/7275* (2013.01); *A61B 5/7465* (2013.01); *A61B 8/08* (2013.01); *A61B 5/4023* (2013.01); *A61B 5/7203* (2013.01); *A61B 5/726* (2013.01);
(Continued)

(58) Field of Classification Search
CPC ..... A61B 5/0002; A61B 5/0015; A61B 5/002; A61B 5/0022; A61B 5/721; A61B 5/11; A61B 5/1113; A61B 5/05; A61B 8/08
See application file for complete search history.

(56) References Cited

U.S. PATENT DOCUMENTS

| | | |
|---|---|---|
| 4,197,537 A | 4/1980 | Follen |
| 4,229,811 A | 10/1980 | Salem |

(Continued)

*Primary Examiner* — Tammie K Heller
(74) *Attorney, Agent, or Firm* — Tran & Associates

(57) ABSTRACT

A monitoring system includes a Doppler radar formed with an IEEE 802 protocol transmitter and an IEEE 802 protocol receiver to detect motion, wherein frequency waves are transmitted by the IEEE 802 protocol transmitter and reflected waves are received by the IEEE protocol 802 receiver; and an analyzer to perform Doppler operations using the IEEE 802 protocol transmitter and receiver, wherein the analyzer calibrates a training Doppler radar signal during a training phase to develop a model and wherein the analyzer applies the model with the Doppler radar signal during an operational phase to determine position.

18 Claims, 7 Drawing Sheets

Related U.S. Application Data continuation of application No. 11/768,381, filed on Jun. 26, 2007, now abandoned.

(60) Provisional application No. 60/939,856, filed on May 24, 2007.

(51) Int. Cl.
*A61B 5/026* (2006.01)
*A61B 5/04* (2006.01)
*A61B 5/0402* (2006.01)
*A61B 5/0476* (2006.01)
*A61B 5/0488* (2006.01)
*A61B 5/107* (2006.01)
*A61B 5/113* (2006.01)
*A61B 8/08* (2006.01)

(52) U.S. Cl.
CPC ....... *A61B 5/7257* (2013.01); *A61B 2560/045* (2013.01); *A61B 2560/0412* (2013.01); *Y10T 307/773* (2015.04)

(56) References Cited

U.S. PATENT DOCUMENTS

| | | |
|---|---|---|
| 4,234,926 A | 11/1980 | Wallace |
| 4,239,961 A | 12/1980 | Lasar |
| 4,275,742 A | 6/1981 | Faisandier |
| 4,310,756 A | 1/1982 | Sick |
| 4,320,767 A | 3/1982 | Villa-Real |
| 4,382,291 A | 5/1983 | Nakauchi |
| 4,384,280 A | 5/1983 | Haag |
| 4,408,224 A | 10/1983 | Yoshida |
| 4,412,545 A | 11/1983 | Okino |
| 4,420,000 A | 12/1983 | Bailey |
| 4,499,564 A | 2/1985 | Sirai |
| 4,514,625 A | 4/1985 | Heiland |
| 4,537,202 A | 8/1985 | Mancini |
| 4,557,270 A | 12/1985 | John |
| 4,595,018 A | 6/1986 | Rantala |
| 4,639,902 A | 1/1987 | Leverance |
| 4,656,319 A | 4/1987 | Bially |
| 4,679,144 A | 7/1987 | Cox |
| 4,722,266 A | 2/1988 | Deckert |
| 4,778,449 A | 10/1988 | Weber |
| 4,807,642 A | 2/1989 | Brown |
| 4,819,648 A | 4/1989 | Ko |
| 4,820,938 A | 4/1989 | Mix |
| 4,862,359 A | 8/1989 | Trivedi |
| 4,869,261 A | 9/1989 | Penaz |
| 4,880,013 A | 11/1989 | Chio |
| 4,907,597 A | 3/1990 | Chamoun |
| 4,922,229 A | 5/1990 | Guenst |
| 4,942,348 A | 7/1990 | Nilssen |
| 4,952,911 A | 8/1990 | D'Ambrosia et al. |
| 4,964,411 A | 10/1990 | Johnson |
| 5,086,385 A | 2/1992 | Launey |
| 5,090,418 A | 2/1992 | Squires |
| RE34,015 E | 8/1992 | Duffy |
| 5,140,990 A | 8/1992 | Jones |
| 5,150,099 A | 9/1992 | Lienau |
| 5,161,529 A | 11/1992 | Stotts |
| 5,162,991 A | 11/1992 | Chio |
| 5,240,487 A | 8/1993 | Kung |
| 5,271,411 A | 12/1993 | Ripley |
| 5,285,793 A | 2/1994 | Slovut |
| 5,287,859 A | 2/1994 | John |
| 5,309,916 A | 5/1994 | Hatschek |
| 5,331,969 A | 7/1994 | Silberstein |
| 5,361,775 A | 11/1994 | Remes |
| 5,364,304 A | 11/1994 | Hampton |
| 5,365,426 A | 11/1994 | Siegel |
| 5,368,039 A | 11/1994 | Moses |
| 5,370,126 A | 12/1994 | Clifford |
| 5,375,610 A | 12/1994 | LaCourse |
| 5,434,419 A | 7/1995 | Decupper |
| 5,435,316 A | 7/1995 | Kruse |
| 5,438,607 A | 8/1995 | Przygoda |
| 5,441,047 A | 8/1995 | David |
| 5,458,620 A | 10/1995 | Adams |
| 5,462,065 A | 10/1995 | Cusimano |
| 5,485,848 A | 1/1996 | Jackson |
| 5,497,781 A | 3/1996 | Chen |
| 5,505,208 A | 4/1996 | Toomim |
| 5,513,651 A | 5/1996 | Cusimano |
| 5,544,649 A | 8/1996 | David |
| 5,544,661 A | 8/1996 | Davis |
| 5,546,953 A | 8/1996 | Garfield |
| 5,551,435 A | 9/1996 | Sramek |
| 5,551,438 A | 9/1996 | Moses |
| 5,579,001 A | 11/1996 | Dempsey |
| 5,579,775 A | 12/1996 | Dempsey |
| 5,584,298 A | 12/1996 | Kabal |
| 5,623,939 A | 4/1997 | Garfield |
| 5,633,910 A | 5/1997 | Cohen |
| 5,652,570 A | 7/1997 | Lepkofker |
| 5,662,118 A | 9/1997 | Skubick |
| 5,671,741 A | 9/1997 | Lang |
| 5,683,425 A | 11/1997 | Hauptmann |
| 5,692,215 A | 11/1997 | Kutzik |
| 5,694,940 A | 12/1997 | Unger |
| 5,708,417 A | 1/1998 | Tallman |
| 5,709,215 A | 1/1998 | Perttu |
| 5,710,551 A | 1/1998 | Ridgeway |
| 5,720,771 A | 2/1998 | Snell |
| 5,722,420 A | 3/1998 | Lee |
| 5,733,230 A | 3/1998 | Sawchuck |
| 5,738,104 A | 4/1998 | Lo |
| 5,738,105 A | 4/1998 | Kroll |
| 5,743,268 A | 4/1998 | Kabal |
| 5,772,603 A | 6/1998 | Ohlsson |
| 5,775,330 A | 7/1998 | Kangas |
| 5,776,073 A | 7/1998 | Garfield |
| 5,785,960 A | 7/1998 | Rigg |
| 5,788,643 A | 8/1998 | Feldman |
| 5,857,975 A | 1/1999 | Golub |
| 5,865,755 A | 2/1999 | Golub |
| 5,876,350 A | 3/1999 | Lo |
| 5,934,362 A | 8/1999 | Barker |
| 5,935,077 A | 8/1999 | Ogle |
| 5,945,112 A | 8/1999 | Flynn |
| 5,964,719 A | 10/1999 | Costello |
| 5,966,090 A | 10/1999 | McEwan |
| 5,967,975 A | 10/1999 | Ridgeway |
| 5,986,600 A | 11/1999 | McEwan |
| 5,987,519 A | 11/1999 | Peifer |
| 5,996,889 A | 12/1999 | Fuchs |
| 6,002,957 A | 12/1999 | Finneran |
| 6,004,312 A | 12/1999 | Finneran |
| 6,010,454 A | 1/2000 | Arieff |
| 6,014,626 A | 1/2000 | Cohen |
| 6,026,987 A | 2/2000 | Burnett |
| 6,032,035 A | 2/2000 | Webster |
| 6,038,469 A | 3/2000 | Karlsson |
| 6,047,202 A | 4/2000 | Finneran |
| 6,050,940 A | 4/2000 | Braun |
| 6,052,619 A | 4/2000 | John |
| 6,056,671 A | 5/2000 | Marmer |
| 6,063,051 A | 5/2000 | Stern |
| 6,070,140 A | 5/2000 | Tran |
| 6,076,011 A | 6/2000 | Hoover |
| 6,108,685 A | 8/2000 | Kutzik |
| 6,171,237 B1 | 1/2001 | Avitall |
| 6,175,308 B1 | 1/2001 | Tallman |
| 6,176,831 B1 | 1/2001 | Voss |
| 6,184,797 B1 | 2/2001 | Stark |
| 6,208,247 B1 | 3/2001 | Agre |
| 6,228,034 B1 | 5/2001 | Voss |
| 6,230,056 B1 | 5/2001 | Kroll |
| 6,246,894 B1 | 6/2001 | Steuer |
| 6,280,393 B1 | 8/2001 | Granger |
| 6,287,252 B1 | 9/2001 | Lugo |
| 6,299,583 B1 | 10/2001 | Eggers |
| 6,331,964 B1 | 12/2001 | Barone |

(56) References Cited

U.S. PATENT DOCUMENTS

| | | |
|---|---|---|
| 6,336,900 B1 | 1/2002 | Alleckson |
| 6,364,834 B1 | 4/2002 | Reuss |
| 6,364,842 B1 | 4/2002 | Amano |
| 6,368,283 B1 | 4/2002 | Xu |
| 6,374,614 B2 | 4/2002 | Prueitt |
| 6,375,614 B1 | 4/2002 | Braun |
| 6,398,727 B1 | 6/2002 | Bui |
| 6,406,426 B1 | 6/2002 | Reuss |
| 6,413,223 B1 | 7/2002 | Yang |
| 6,416,480 B1 | 7/2002 | Nenov |
| 6,433,690 B2 | 8/2002 | Petelenz |
| 6,440,067 B1 | 8/2002 | DeLuca |
| 6,443,906 B1 | 9/2002 | Ting |
| 6,445,299 B1 | 9/2002 | Rojas |
| 6,466,816 B2 | 10/2002 | Granger |
| 6,473,640 B1 | 10/2002 | Erlebacher |
| 6,475,146 B1 | 11/2002 | Freiburger |
| 6,475,153 B1 | 11/2002 | Khair |
| 6,487,442 B1 | 11/2002 | Wood |
| 6,514,211 B1 | 2/2003 | Baura |
| 6,515,593 B1 | 2/2003 | Stark |
| 6,533,729 B1 | 3/2003 | Khair |
| 6,544,173 B2 | 4/2003 | West |
| 6,544,174 B2 | 4/2003 | West |
| 6,546,269 B1 | 4/2003 | Kurnik |
| 6,554,774 B1 | 4/2003 | Miele |
| 6,556,860 B1 | 4/2003 | Groenewegen |
| 6,595,316 B2 | 7/2003 | Cybulski |
| 6,597,944 B1 | 7/2003 | Hadas |
| 6,605,038 B1 | 8/2003 | Teller |
| 6,609,023 B1 | 8/2003 | Fischell |
| 6,612,984 B1 | 9/2003 | Kerr |
| 6,615,074 B2 | 9/2003 | Mickle |
| 6,615,075 B2 | 9/2003 | Mlynash |
| 6,616,613 B1 | 9/2003 | Goodman |
| 6,660,042 B1 | 12/2003 | Curcie |
| 6,661,161 B1 | 12/2003 | Lanzo |
| 6,676,600 B1 | 1/2004 | Conero |
| 6,678,549 B2 | 1/2004 | Cusimano |
| 6,678,551 B2 | 1/2004 | Maalouf |
| 6,687,519 B2 | 2/2004 | Steuer |
| 6,705,990 B1 | 3/2004 | Gallant |
| 6,720,984 B1 | 4/2004 | Jorgensen |
| 6,730,038 B2 | 5/2004 | Gallant |
| 6,740,045 B2 | 5/2004 | Amano |
| 6,747,561 B1 | 6/2004 | Reeves |
| 6,760,620 B2 | 7/2004 | Sippens Groenewegen |
| 6,783,492 B2 | 8/2004 | Dominguez |
| 6,804,656 B1 | 10/2004 | Rosenfeld |
| 6,816,266 B2 | 11/2004 | Varshneya |
| 6,829,501 B2 | 12/2004 | Nielsen |
| 6,832,251 B1 | 12/2004 | Gelvin |
| 6,834,436 B2 | 12/2004 | Townsend |
| 6,843,771 B2 | 1/2005 | Lo |
| 6,856,291 B2 | 2/2005 | Mickle |
| 6,865,409 B2 | 3/2005 | Getsla |
| 6,871,211 B2 | 3/2005 | Labounty |
| 6,882,128 B1 | 4/2005 | Rahmel |
| 6,887,202 B2 | 5/2005 | Currie |
| 6,898,460 B2 | 5/2005 | Hoctor |
| 6,907,288 B2 | 6/2005 | Daum |
| 6,912,420 B2 | 6/2005 | Scheiner |
| 6,944,496 B2 | 9/2005 | Jeong |
| 6,961,285 B2 | 11/2005 | Niemiec |
| 6,965,794 B2 | 11/2005 | Brody |
| 6,973,344 B2 | 12/2005 | Finneran |
| 6,974,419 B1 | 12/2005 | Voss |
| 6,975,206 B2 | 12/2005 | Reining |
| 6,980,852 B2 | 12/2005 | Jersey-Willuhn |
| 6,989,751 B2 | 1/2006 | Richards |
| 7,004,907 B2 | 2/2006 | Banet |
| 7,009,519 B2 | 3/2006 | Leonard |
| 7,011,629 B2 | 3/2006 | Bulat |
| 7,035,679 B2 | 4/2006 | Addison |
| 7,043,293 B1 | 5/2006 | Baura |
| 7,884,727 B2 | 2/2011 | Tran |
| 8,249,731 B2 | 8/2012 | Tran |
| 2002/0120184 A1 | 8/2002 | Beck |
| 2003/0004421 A1 | 1/2003 | Ting |
| 2003/0125635 A1 | 7/2003 | Maalouf |
| 2003/0135127 A1 | 7/2003 | Sackner |
| 2003/0216630 A1 | 11/2003 | Jersey-Willuhn |
| 2003/0216662 A1 | 11/2003 | Jersey-Willuhn |
| 2003/0216663 A1 | 11/2003 | Jersey-Willuhn |
| 2003/0231115 A1 | 12/2003 | Stanners |
| 2004/0044273 A1 | 3/2004 | Keith |
| 2004/0095237 A1 | 5/2004 | Chen |
| 2004/0102683 A1 | 5/2004 | Khanuja |
| 2004/0122487 A1 | 6/2004 | Hatlestad |
| 2004/0138568 A1 | 7/2004 | Lo |
| 2004/0152957 A1 | 8/2004 | Stivoric |
| 2004/0167409 A1 | 8/2004 | Lo |
| 2004/0167417 A1 | 8/2004 | Schulhauser |
| 2004/0217881 A1 | 11/2004 | Pedyash |
| 2004/0220490 A1 | 11/2004 | Appel et al. |
| 2004/0223891 A1 | 11/2004 | Brown |
| 2004/0254493 A1 | 12/2004 | Chervin |
| 2004/0260188 A1 | 12/2004 | Syed |
| 2004/0267148 A1 | 12/2004 | Arand |
| 2005/0038345 A1 | 2/2005 | Gorgenberg |
| 2005/0055568 A1 | 3/2005 | Agrawala |
| 2005/0061568 A1 | 3/2005 | Schondorf |
| 2005/0073424 A1 | 4/2005 | Ruoss |
| 2005/0099387 A1 | 5/2005 | Matsumoto |
| 2005/0113630 A1 | 5/2005 | Fox |
| 2005/0113710 A1 | 5/2005 | Stahmann |
| 2005/0115561 A1 | 6/2005 | Stahmann |
| 2005/0143667 A1 | 6/2005 | Park |
| 2005/0148882 A1 | 7/2005 | Banet |
| 2005/0164675 A1 | 7/2005 | Tuulos |
| 2005/0185575 A1 | 8/2005 | Hansen |
| 2005/0194926 A1 | 9/2005 | Di Stefano |
| 2005/0201585 A1 | 9/2005 | Jannard |
| 2005/0209521 A1 | 9/2005 | Kettunen |
| 2005/0222515 A1 | 10/2005 | Polyshchuk |
| 2005/0228244 A1 | 10/2005 | Banet |
| 2005/0228299 A1 | 10/2005 | Banet |
| 2005/0228316 A1 | 10/2005 | Morgenstern |
| 2005/0240086 A1 | 10/2005 | Akay |
| 2005/0240523 A1 | 10/2005 | Richardson |
| 2005/0240758 A1 | 10/2005 | Lord |
| 2005/0245831 A1 | 11/2005 | Banet |
| 2005/0261594 A1 | 11/2005 | Banet |
| 2005/0261598 A1 | 11/2005 | Banet |
| 2005/0278409 A1 | 12/2005 | Kutzik |
| 2006/0009697 A1 | 1/2006 | Banet |
| 2006/0009698 A1 | 1/2006 | Banet |
| 2006/0028997 A1 | 2/2006 | McFarland |
| 2006/0047215 A1 | 3/2006 | Newman |
| 2006/0079801 A1 | 4/2006 | DeLuca |
| 2006/0082727 A1 | 4/2006 | Bolger |
| 2006/0084878 A1 | 4/2006 | Banet |
| 2006/0094975 A1 | 5/2006 | Manto |
| 2006/0105357 A1 | 5/2006 | Benesch |
| 2006/0132303 A1 | 6/2006 | Stilp |
| 2006/0167346 A1 | 7/2006 | Sarel |
| 2006/0291575 A1 | 12/2006 | Berkman |
| 2007/0085690 A1 | 4/2007 | Tran |
| 2007/0183329 A1 | 8/2007 | Elwell |
| 2007/0220907 A1 | 9/2007 | Ehlers |
| 2007/0236946 A1 | 10/2007 | Petrakis |
| 2007/0271006 A1 | 11/2007 | Golden |
| 2008/0003938 A1 | 1/2008 | Baruschke |
| 2008/0055108 A1 | 3/2008 | Han |
| 2008/0077015 A1* | 3/2008 | Boric-Lubecke .... A61B 5/0205 600/453 |
| 2008/0157965 A1 | 7/2008 | Shahar |
| 2008/0183307 A1 | 7/2008 | Clayton |
| 2008/0248808 A1* | 10/2008 | Alizadeh-Shabdiz H04W 64/006 455/456.1 |
| 2008/0266050 A1 | 10/2008 | Crouse |
| 2009/0187499 A1 | 7/2009 | Mulder |
| 2009/0216528 A1 | 8/2009 | Gemello |
| 2010/0012737 A1 | 1/2010 | Kates |

(56) References Cited

U.S. PATENT DOCUMENTS

| | | |
|---|---|---|
| 2010/0026479 A1 | 2/2010 | Tran |
| 2010/0146712 A1 | 6/2010 | Finch |
| 2010/0243754 A1 | 9/2010 | Harris |
| 2011/0025497 A1 | 2/2011 | Zaveruha |
| 2011/0121664 A1 | 5/2011 | Voisine |
| 2011/0269389 A1 | 11/2011 | Scharf |

\* cited by examiner

| |
|---|
| Set up mesh network appliances with one transmitter and one receiver (1000) |
| Determine chest movement using Doppler principle to infer vital signs such as heart activity (1002) |
| Determine patient movement (1004) |
| Determine vital parameter including patient heart rate (1006) |
| Determine if patient needs assistance based on in-door position, fall detection and vital sign parameter (1008) |
| Confirm prior to calling third party (1010) |
| If confirmed or non-responsive, make connection with third party and send voice over mesh network to appliance worn by the patient (1012) |
| If needed, call emergency personnel to get medical care (1014) |

FIG. 2

| |
|---|
| Detect weakness in left half and right half of patient body - arms, legs, face (3000) |
| Detect walking pattern for loss of balance or coordination (3002) |
| Ask user to move hands/feet in a predetermined pattern (3004) |
| Read accelerometer output in accordance with predetermined pattern movement (3006) |
| Provide accelerometer output to a pattern classifier (3008) |
| Check whether patient is experiencing dizziness or sudden, severe headache with no known cause (3010) |
| Display a text image and ask the patient to read back the text image, one eye at a time (3012) |
| Use speech recognizer to detect confusion, trouble speaking or understanding (3014) |
| Ask patient if they feel numbness in the body- arms, legs, face (3016) |
| Ask patient to squeeze gauge/force sensor to determine force applied during squeeze (3018) |

FIG. 4C

| |
|---|
| Compare historical left shoulder (LS) strength against current LS strength (3200) |
| Compare historical right shoulder (RS) strength against current RS strength (3202) |
| Compare historical left hip (LH) strength against current LH strength (3204) |
| Compare historical right hip (RH) strength against current RH strength (3206) |
| If variance between historical and current strength exceeds threshold, generate warning (3208) |

FIG. 4E

WIRELESS MONITORING

CROSS REFERENCE TO RELATED APPLICATIONS

This application is a continuation of U.S. application Ser. No. 11/832,735 filed Aug. 2, 2007, now issued as U.S. Pat. No. 8,750,971, the contents of which are incorporated by reference.

BACKGROUND

This invention relates generally to methods and systems for monitoring a person.

RF transceivers are commonly available as WiFi or WiMAX® transceivers for wireless data transmission. On a parallel note, there is a need to track people using wireless transmitter and receivers.

SUMMARY

In one aspect, a monitoring system includes a Doppler radar formed with an IEEE 802 protocol transmitter and an IEEE 802 protocol receiver to detect motion, wherein frequency waves are transmitted by the IEEE 802 protocol transmitter and reflected waves are received by the IEEE protocol 802 receiver; and an analyzer to perform Doppler operations using the IEEE 802 protocol transmitter and receiver, wherein the analyzer calibrates a training Doppler radar signal during a training phase to develop a model and wherein the analyzer applies the model with the Doppler radar signal during an operational phase to determine position.

In another aspect, a heart monitoring system includes an 802 protocol transmitter; an 802 protocol receiver adapted to communicate with the 802 transmitter, the 802 protocol transmitter and receiver forming a Doppler radar to detect heartbeat motion on a chest; and an analyzer coupled to one of the transmitter and receiver to determine heart attack or stroke attack.

In another aspect, a monitoring system for a person includes a wireless local area network (WLAN) transceivers operating as a Doppler radar to wirelessly detect the person's heart parameter such as heart rate; and a processor coupled to the WLAN transceivers to determine a stroke attack.

In yet another aspect, a health care monitoring system for a person includes one or more wireless nodes forming a wireless mesh network; WLAN transceivers operating as a Doppler radar to detect heart beat; and a processor coupled to the WLAN transceivers to detect a heart attack or a stroke attack.

In another aspect, a monitoring system for a person includes one or more wireless nodes and a stroke sensor coupled to the person and the wireless nodes to determine a stroke attack.

In another aspect, a health care monitoring system for a person includes one or more wireless nodes forming a wireless mesh network; a wearable appliance having a sound transducer coupled to the wireless transceiver; and a bio-electric impedance (BI) sensor coupled to the wireless mesh network to communicate BI data over the wireless mesh network.

In a further aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth.

In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected.

In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected.

Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VoIP) code to allow a user and a remote person to audibly communicate with each other. The voice communication system can include Zigbee® VoIP or Bluetooth® VoIP or 802.XX VoIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected. The system can also perform calibrating Doppler radar signal with an actual blood pressure during a training phase to develop a model and using the model with Doppler radar signal during an operational phase to estimate continuous blood pressure.

In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected.

In yet another aspect, a monitoring system includes one or more cameras to determine a three dimensional (3D) model of a person; means to detect a dangerous condition based on the 3D model; and means to generate a warning when the dangerous condition is detected.

In another aspect, a method to detect a dangerous condition for an infant includes placing a pad with one or more sensors in the infant's diaper; collecting infant vital parameters; processing the vital parameter to detect SIDS onset; and generating a warning.

In yet another embodiment, a wireless housing provides one or more bioelectric contacts conveniently positioned to collect bioelectric patient data. The housing can be a patch, a wristwatch, a band, a wristband, a chest band, a leg band, a sock, a glove, a foot pad, a head-band, an ear-clip, an ear phone, a shower-cap, an armband, an ear-ring, eye-glasses, sun-glasses, a belt, a sock, a shirt, a garment, a jewelry, a bed spread, a pillow cover, a pillow, a mattress, a blanket or a sleeping garment such as a pajama. The bed spread, pillow cover, pillow, mattress, blanket or pajama can have bioelectrically conductive contacts in an array so that the patient can enjoy his/her sleep while vital parameters can be captured. In one embodiment, an array of parallel conductive lines can be formed on the housing side that faces the patient and the electrical signal can be picked up. The data captured by the contacts are transmitted over the mesh network such as Zigbee® to a base station.

In the above embodiments, the base station can perform the bioelectric signal processing to extract patient parameters from data captured by the contacts. In this case, the base station may need a DSP or powerful CPU to perform the calculations. Alternatively, in an ASP model, the base station can simply compress the data and upload the data to a central server or server farm for processing and the result of the signal processing are sent back to the base station for relay to the patient interface which can be a wrist-watch, a pad, or a band, among others, for notification of any warning signs.

Advantages of the system may include one or more of the following. The system detects the warning signs of stroke and prompts the user to reach a health care provider within a few hours of symptom onset. The system enables patent to properly manage acute stroke, and the resulting early treatment might reduce the degree of morbidity that is associated with first-ever strokes.

Other advantages of the invention may include one or more of the following. The system for non-invasively and continually monitors a subject's arterial blood pressure, with reduced susceptibility to noise and subject movement, and relative insensitivity to placement of the apparatus on the subject. The system does not need frequent recalibration of the system while in use on the subject. The Doppler detection of heart rate and blood flow can be used to monitor patients without requiring them to wear or embed any medical device on the body.

In particular, it allows patients to conduct a low-cost, comprehensive, real-time monitoring of their blood pressure. Using the web services software interface, the invention then avails this information to hospitals, home-health care organizations, insurance companies, pharmaceutical agencies conducting clinical trials and other organizations. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

In certain embodiments that supplement the Doppler radar with wearable appliance, such appliance is small, easily worn by the patient during periods of exercise or day-to-day activities, and non-invasively measures blood pressure can be done in a matter of seconds without affecting the patient. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

When used in conjunction with the Doppler radar, the wearable appliance provides an in-depth, cost-effective mechanism to evaluate a patient's cardiac condition. Certain cardiac conditions can be controlled, and in some cases predicted, before they actually occur. Moreover, data from the patient can be collected and analyzed while the patient participates in their normal, day-to-day activities.

In cases where the device has fall detection in addition to blood pressure measurement, other advantages of the invention may include one or more of the following. The system provides timely assistance and enables elderly and disabled individuals to live relatively independent lives. The system monitors physical activity patterns, detects the occurrence of falls, and recognizes body motion patterns leading to falls. Continuous monitoring of patients is done in an accurate, convenient, unobtrusive, private and socially acceptable manner since a computer monitors the images and human involvement is allowed only under pre-designated events. The patient's privacy is preserved since human access to videos of the patient is restricted: the system only allows human viewing under emergency or other highly controlled conditions designated in advance by the user. When the patient is healthy, people cannot view the patient's video without the patient's consent. Only when the patient's safety is threatened would the system provide patient information to authorized medical providers to assist the patient. When an emergency occurs, images of the patient and related medical data can be compiled and sent to paramedics or hospital for proper preparation for pick up and check into emergency room.

The system allows certain designated people such as a family member, a friend, or a neighbor to informally check on the well-being of the patient. The system is also effective in containing the spiraling cost of healthcare and outpatient care as a treatment modality by providing remote diagnostic capability so that a remote healthcare provider (such as a doctor, nurse, therapist or caregiver) can visually communicate with the patient in performing remote diagnosis. The system allows skilled doctors, nurses, physical therapists, and other scarce resources to assist patients in a highly efficient manner since they can do the majority of their functions remotely.

Additionally, a sudden change of activity (or inactivity) can indicate a problem. The remote healthcare provider may receive alerts over the Internet or urgent notifications over the phone in case of such sudden accident indicating changes. Reports of health/activity indicators and the overall well being of the individual can be compiled for the remote healthcare provider. Feedback reports can be sent to monitored subjects, their designated informal caregiver and their remote healthcare provider. Feedback to the individual can encourage the individual to remain active. The content of the report may be tailored to the target recipient's needs, and can present the information in a format understandable by an elder person unfamiliar with computers, via an appealing patient interface. The remote healthcare provider will have access to the health and well-being status of their patients without being intrusive, having to call or visit to get such information interrogatively. Additionally, remote healthcare provider can receive a report on the health of the monitored subjects that will help them evaluate these individuals better during the short routine check up visits. For example, the system can perform patient behavior analysis such as eating/drinking/smoke habits and medication compliance, among others.

The patient's home equipment is simple to use and modular to allow for the accommodation of the monitoring device to the specific needs of each patient. Moreover, the system is simple to install. Regular monitoring of the basic wellness parameters provides significant benefits in helping to capture adverse events sooner, reduce hospital admissions, and improve the effectiveness of medications, hence, lowering patient care costs and improving the overall quality of care. Suitable users for such systems are disease management companies, health insurance companies, self-insured employers, medical device manufacturers and pharmaceutical firms.

The system reduces costs by automating data collection and compliance monitoring, and hence reduce the cost of nurses for hospital and nursing home applications. At-home vital signs monitoring enables reduced hospital admissions and lower emergency room visits of chronic patients. Operators in the call centers or emergency response units get high quality information to identify patients that need urgent care so that they can be treated quickly, safely, and cost effectively. The Web based tools allow easy access to patient information for authorized parties such as family members, neighbors, physicians, nurses, pharmacists, caregivers, and other affiliated parties to improved the Quality of Care for the patient.

In an on-line pharmacy aspect, a method for providing patient access to medication includes collecting patient medical information from a patient computer; securing the patient medical information and sending the secured patient medical information from the patient computer to a remote computer; remotely examining the patient and reviewing the patient medical information; generating a prescription for the patient and sending the prescription to a pharmacy; and performing a drug interaction analysis on the prescription.

Implementations of the on-line pharmacy aspect may include one or more of the following. The medical information can include temperature, EKG, blood pressure, weight, sugar level, image of the patient, or sound of the patient. Responses from the patient to a patient medical questionnaire can be captured. The doctor can listen to the patient's organ with a digital stethoscope, scanning a video of the patient, running a diagnostic test on the patient, verbally communicating with the patient. The digital stethoscope can be a microphone or piezoelectric transducer coupled to the Zigbee® network to relay the sound. A plurality of medical rules can be applied to the medical information to arrive at a diagnosis. Genetic tests or pharmacogenetic tests can be run on the patient to check compatibility with the prescription. Approval for the prescription can come from one of: a doctor, a physician, a physician assistant, a nurse. The system can monitor drug compliance, and can automatically ordering a medication refill from the pharmacy.

For pharmacy applications, advantages of the pharmacy system may include one or more of the following. The system shares the patient's medical history and can be updated by a remote physician and the remote dispensing pharmacy. As the doctor and the pharmacy have the same access to the patient medical history database, patient data is updated in real time, and is as current and complete as possible. The patient, doctor, pharmacy, and third party testing entities benefit from a uniform pricing structure that is based on the diagnosis and treatment. The patient only pays for standard medical treatments for his or her illness. The physician is paid a standard fee which covers the average work spent with a patient with the specific type of medical situation. The dispensing pharmacy is able to provide the highest level of service, since it is able to double check all medications dispensed to each patient along with the optimal way to detect anticipated negative drug interactions. The pricing structure is competitive as physicians do not need to be distributed physically, and those with specialty areas may remain centrally located and yet be able to interact electronically with patients. The system still provides physical access to specialists since the patients which are evaluated can be directed to visit a specialists physically, when remote review and contact is ineffectual. The on-line pharmacy tracks the specific needs and medical history of each patient and can provide an expert system to advise the patient on proper drug usage and potential drug interactions. The system automates the purchasing of drugs, pricing the prescription or submission of the claims to a third party for pricing, entering the complete prescription in their computer system, and auditing from third parties which provide payment. The on-line pharmacy provides detailed multimedia guidance or assistance to the patient regarding the filled prescription. The patient can freely search for answers regarding the use of the filled prescription, its possible side effects, possible interactions with other drugs, possible alternative treatments, etc. The patient can communicate using video or VoIP with a remote pharmacist regarding any number of questions, and be counseled by the local pharmacist on the use of the filled prescription. Thus, the system minimizes the danger from harmful side effects or drug interactions by providing patients with full access to information. The system allows a patient to enjoy the selection and price of a mail-order pharmacy without subjecting the patient to dangerous interactions or side effects which may occur in unsupervised prescription purchases. The on-line pharmacy offers the selection and benefits of a "central fill" pharmacy method without requiring the local pharmacy to purchase drugs to fill each prescription, price each prescription, or be subjected to audits from third parties who provide payment.

BRIEF DESCRIPTION OF THE DRAWINGS

FIG. 2 illustrates an exemplary process for determining and getting assistance for a patient or user.

FIGS. 4C-4E shows exemplary stroke determination processes.

DESCRIPTION

Figure 1:
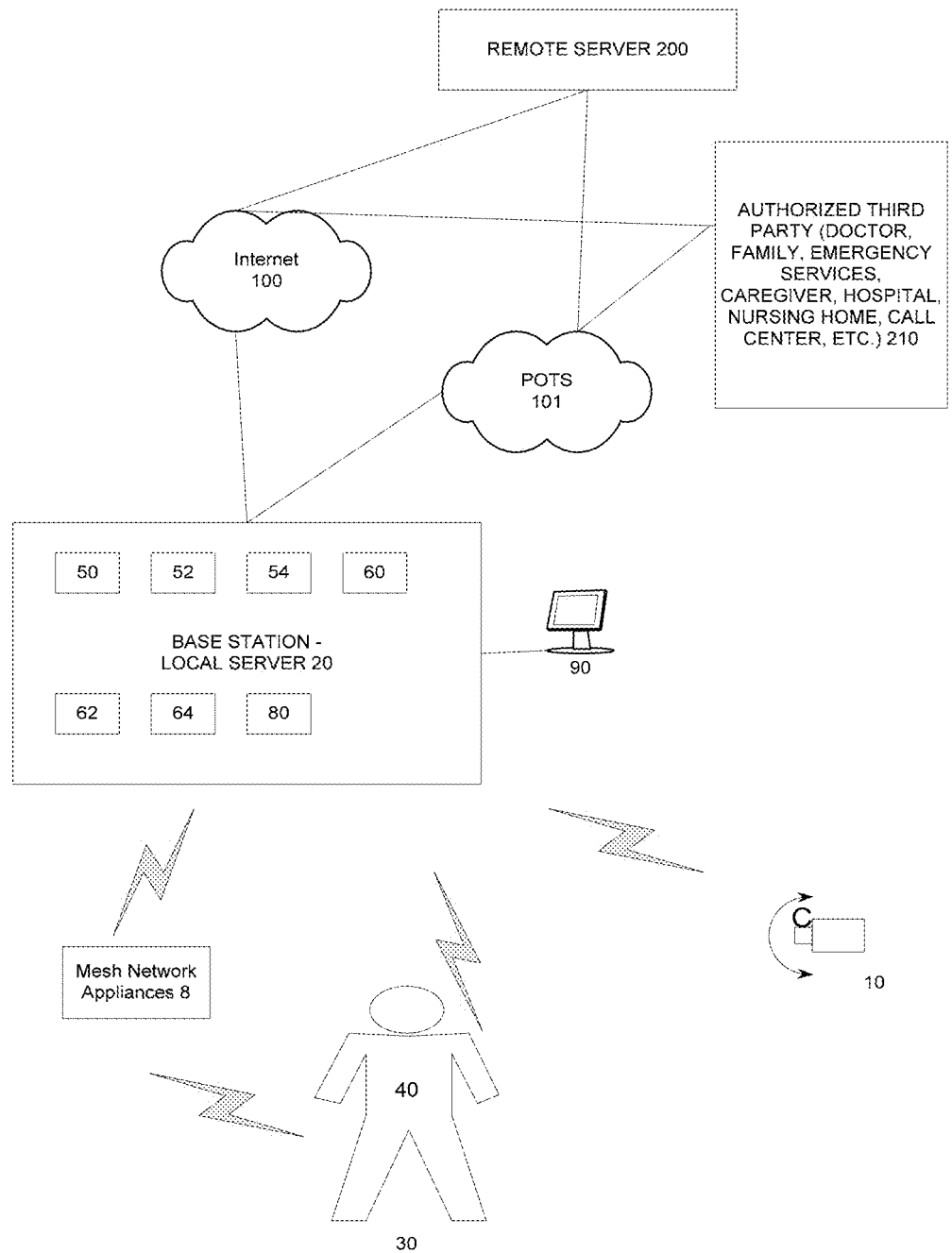
FIG. 1 illustrates an exemplary system for monitoring a person.

FIG. 1 shows an exemplary patient monitoring system. The system can operate in a home, a nursing home, or a hospital. In this system, one or more mesh network appliances 8 are provided to enable wireless communication in the home monitoring system. Appliances 8 in the mesh network can include home security monitoring devices, door alarm, window alarm, home temperature control devices, fire alarm devices, among others. Appliances 8 in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine on exercise parameters such as distance, time, and heart rate.

Figure 3:
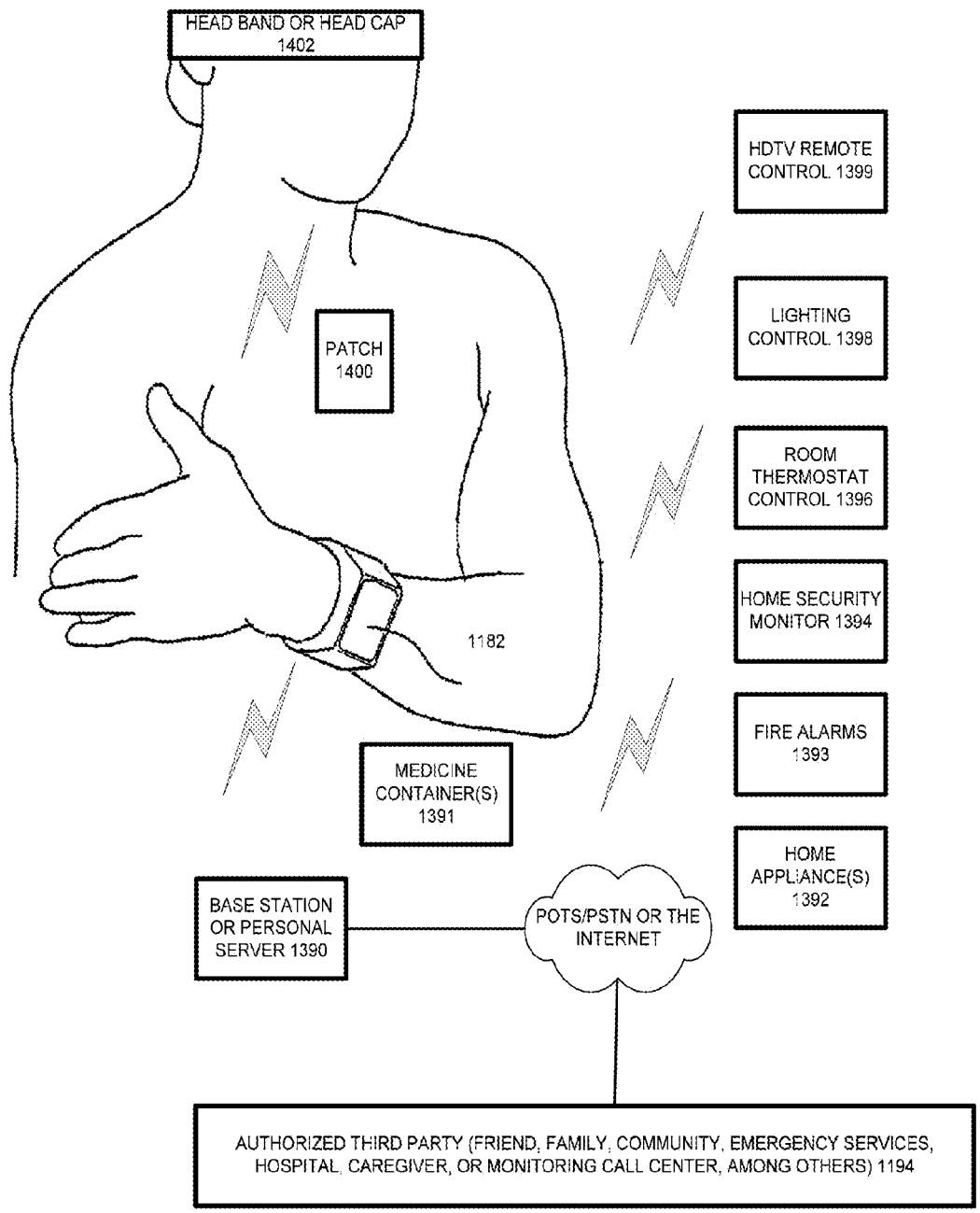
FIG. 3 shows an exemplary network.

As will be discussed in more detail below, one appliance is a patient monitoring device that can be worn by the patient and includes a single or bi-directional wireless communication link, generally identified by the bolt symbol in FIG. 1, for transmitting data from the appliances 8 to the local hub or receiving station or base station server 20 by way of a wireless radio frequency (RF) link using a proprietary or non-proprietary protocol. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Zigbee® network or 802.15 network. More details of the mesh network is shown in FIG. 3 and discussed in more detail below.

Another appliance can be a Doppler sensor that senses heart rate and/or EKG signals generated by the patient without requiring the patient to wear anything. In this system, one or more wireless nodes form a wireless mesh network; and each node can contain a wireless transceiver that cooperate with other transceivers to form a Doppler radar to detect heart motion. From the heart motion data, an analyzer determines heart attack or stroke attack without requiring the patient to wear electronics. The analyzer communicates with the wireless transceivers to receive patient data over the wireless mesh network.

In one embodiment, two 802.X protocol LAN wireless adapters are used: one as a transmitter and the other one as a receiver. Antennas operate as separate transmit and receive antennas for performing transmission and reception simultaneously during the process of wirelessly measuring heart beat. Each LAN wireless adapter can be an 802.16 (WiMAX®), 802.15 (Zigbee®) or 802.11 (WiFi) adapter that can be wall mounted or placed on suitable furniture.

Another embodiment uses a multiple input, multiple output (MIMO) wireless adapter chip set with four antennas and two radios such as the WiMAX® MIMO transceiver UXA23465 from NXP with a suitable baseband ASIC which send data over two transceivers simultaneously. The inventor contemplates that the adapter can also be 802.11 (WiFi), 802.15 (Zigbee®) or Bluetooth® adapters.

The local oscillators of the adapters are synchronized by providing a common crystal reference to the LO synthesizers in both cards. The baseband output of the receiver adapter is prefiltered with a low-pass RC filter with a cut-off frequency of 100 Hz to remove out of band noise and avoid aliasing error. The pre-filtered signal is digitized and used to calculate heart rate. The digitized signal is the additionally filtered in the digital domain to separate the heart and breathing signals. To determine heart rate, an autocorrelation function was calculated for the heart signal. The periodicity of the autocorrelation function is used to determine the heart rate. A filter can also be applied to extract breathing rate from the digitized signal.

In the Doppler radar phenomenon, the frequency of a radio signal is altered when the signal reflects off of a moving object. The periodic movement of the chest and internal organs modulates an incident or transmitted radio signal from one of the wireless transceivers, and the resulting reflection is interpreted to deduce, for example, heart and breathing activity. In one embodiment, the system uses WiMAX® transceivers which operate at higher frequencies, around 5-6 GHz and which provide high resolution and improved antenna patterns could be used for more detailed observations of arterial motion.

When a radio wave reflects off a moving object, its frequency changes—a phenomenon called the Doppler effect. The system identifies frequency changes to detect moving objects. It's about the size of a suitcase and contains a radio receiver composed of two antennas—and a signal-processing unit. The system can determine a person's location, speed and direction—even through a one-foot-thick brick wall.

When Wi-Fi radio waves bounce off a moving object, their frequency changes. If, for example, a person is moving toward the Wi-Fi source, the reflected waves' frequency increases. If a person is moving away from the source, the frequency decreases. A Wi-Fi Internet router already in the room fills the area with radio waves of a specific frequency, usually 2.4 or 5 gigahertz. One antenna of the radar system tracks the baseline radio signal in the room. A second antenna detects radio waves that have reflected off of moving objects, which changes their frequency. By comparing the two antennas' signals, the computer calculates the object's location to within a few feet as well as its speed and direction.

Because the device itself doesn't emit any radio waves, it can't be detected. The Wi-Fi radar could have domestic applications ranging from spotting intruders to unobtrusively monitoring children or the elderly. The system can be used to scan buildings during urban warfare.

The non-invasive measuring techniques according to the present invention can be enhanced by the attachment of wireless sensors to critical locations on the body. The body sensor technique allows the return or reflected signal to be more easily isolated from radar clutter effects, and provides a means for sensing additional data not easily derived from a radar signal, such as skin temperature. The body sensors can be as simple as conductive patches that attach to the skin and enhance the reflection of the incident radio signal at a particular location. Alternatively, the body sensors are more complex frequency resonant structures, or even oscillating or multiplying semiconductor circuits. Such circuits can alter the reflected radio signal in time and/or frequency, and can impose additional modulated data, which is generated by, for example, skin temperature, bioelectric effects, re-radiated radar effects, and physical acceleration.

A conducting surface will then reflect most of the energy from an incident radio wave. Placing such a surface or patch on a target area of the body, such as the chest or the skin over an artery, will enhance the return of the radar signal from that target area. As one skilled in the art will appreciate, if the physical dimensions of the conducting surface are properly chosen, the path can act as an electrically resonant antenna that provides an enhanced radar return.

In one embodiment, each person's heartbeat is a virtual fingerprint that can be used to identify one person from another person in the house. As discussed above, suitable statistical recognizers such as Hidden Markov Model (HMM) recognizers, neural network, fuzzy recognizer, dynamic time warp (DTW) recognizer, a Bayesian network, or a Real Analytical Constant Modulus Algorithm (RACMA) recognizer, among others can be used to distinguish one person's heartbeat from another. This technique allows the system to track multiple people in a residence at once. Additionally, three or more transceivers can be positioned in the residence so that their position can be determined through triangulation. The positional data, heart rate, and breathing rate/respiration rate, as well as change delta for each, can be data mined to determine the user's daily activity patterns. A Hidden Markov Model (HMM) recognizer, a dynamic time warp (DTW) recognizer, a neural network, a fuzzy logic engine, or a Bayesian network can be applied to the actual or the difference/change for a particular signal, for example the heart rate or breathing rate, to determine the likelihood of a stroke attack in one embodiment. In another embodiment, the Doppler radar picks up S1-S4 heart sounds as discussed below and determine the likelihood of a stroke from the heart sound patterns for S1-S4.

A plurality of monitoring cameras 10 may be placed in various predetermined positions in a home of a patient 30. The cameras 10 can be wired or wireless. For example, the cameras can communicate over infrared links or over radio links conforming to the 802x (e.g. 802.11A, 802.11B, 802.11G, 802.15) standard or the Bluetooth® standard to a base station/server 20 may communicate over various communication links, such as a direct connection, such a serial connection, USB connection, Firewire connection or may be optically based, such as infrared or wireless based, for example, home RF, IEEE standard 802.11a/b, Bluetooth® or the like. In one embodiment, appliance 8 monitors the patient and activates the camera 10 to capture and transmit video to an authorized third party for providing assistance should the appliance 8 detects that the user needs assistance or that an emergency had occurred.

The base station/server 20 stores the patient's ambulation pattern and vital parameters and can be accessed by the patient's family members (sons/daughters), physicians, caretakers, nurses, hospitals, and elderly community. The base station/server 20 may communicate with the remote server 200 by DSL, T-1 connection over a private communication network or a public information network, such as the Internet 100, among others.

Although the Doppler radar system can operate without requiring the patient to wear the measuring devices thereon, the patient 30 may still wear one or more wearable patient monitoring appliances such as wrist-watches or clip on devices or electronic jewelry to monitor the patient. When used in conjunction with the Doppler radar, one wearable appliance such as a wrist-watch includes sensors 40, for example devices for sensing ECG, EKG, blood pressure, sugar level, among others. In one embodiment, the sensors 40 are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors 40 can individually transmit data to the server 20 using wired or wireless transmission. Alternatively, all sensors 40 can be fed through a common bus into a single transceiver for wired or wireless transmission. The transmission can be done using a magnetic medium such as a floppy disk or a flash memory card, or can be done using infrared or radio network link, among others. The sensor 40 can also include an indoor positioning system or alternatively a global position system (GPS) receiver that relays the position and ambulatory patterns of the patient to the server 20 for mobility tracking.

In one embodiment, the sensors 40 for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of a unit such as clothing, underwear or wearable electronics such as a wrist-watch case. In the case of a garment, a piezoelectric transducer is placed on the back of the garment. As the user breathes, the piezoelectric transducer is stretched and the resulting piezo output is used to detect breathing rate and heart rate, among others. In yet another embodiment that provides continuous, beat-to-beat wrist arterial pulse rate measurements, a pressure sensor is housed in a wrist mounted casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The case may be of a number of variations of shape but can be conveniently made a rectangular, approaching a box-like configuration. The wrist-band can be an expansion band or a wristwatch strap of plastic, leather or woven material. The wrist-band further contains an antenna for transmitting or receiving radio frequency signals. The wrist-band and the antenna inside the band are mechanically coupled to the top and bottom sides of the wrist-watch housing. Further, the antenna is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission.

In another embodiment, the sensors 40 are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure.

In another embodiment, instead of being mounted on the patient, the sensors can be mounted on fixed surfaces such as walls or tables, for example. One such sensor is a motion detector. Another sensor is a proximity sensor. The fixed sensors can operate alone or in conjunction with the cameras 10. In one embodiment where the motion detector operates with the cameras 10, the motion detector can be used to trigger camera recording. Thus, as long as motion is sensed, images from the cameras 10 are not saved. However, when motion is not detected, the images are stored and an alarm may be generated. In another embodiment where the motion detector operates stand alone, when no motion is sensed, the system generates an alarm.

The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

The system can also monitor the patient's gait pattern and generate warnings should the patient's gait patterns indicate that the patient is likely to fall. The system will detect patient skeleton structure, stride and frequency; and based on this information to judge whether patient has joint problem, asymmetrical bone structure, among others. The system can store historical gait information, and by overlaying current structure to the historical (normal) gait information, gait changes can be detected. In the camera embodiment, an estimate of the gait pattern is done using the camera. In a camera-less embodiment, the gait can be sensed by providing a sensor on the floor and a sensor near the head and the variance in the two sensor positions are used to estimate gait characteristics.

The system also provides a patient interface 90 to assist the patient in easily accessing information. In one embodiment, the patient interface includes a touch screen; voice-activated text reading; one touch telephone dialing; and video conferencing. The touch screen has large icons that are pre-selected to the patient's needs, such as his or her favorite web sites or application programs. The voice activated text reading allows a user with poor eye-sight to get information from the patient interface 90. Buttons with pre-designated dialing numbers, or video conferencing contact information allow the user to call a friend or a healthcare provider quickly.

In one embodiment, medicine for the patient is tracked using radio frequency identification (RFID) tags. In this embodiment, each drug container is tracked through an RFID tag that is also a drug label. The RF tag is an integrated circuit that is coupled with a mini-antenna to transmit data. The circuit contains memory that stores the identification Code and other pertinent data to be transmitted when the chip is activated or interrogated using radio energy from a reader. A reader consists of an RF antenna, transceiver and a micro-processor. The transceiver sends activation signals to and receives identification data from the tag. The antenna may be enclosed with the reader or located outside the reader as a separate piece. RFID readers communicate directly with the RFID tags and send encrypted usage data over the patient's network to the server 200 and eventually over the Internet 100. The readers can be built directly into the walls or the cabinet doors.

In one embodiment, capacitively coupled RFID tags are used. The capacitive RFID tag includes a silicon microprocessor that can store 96 bits of information, including the pharmaceutical manufacturer, drug name, usage instruction and a 40-bit serial number. A conductive carbon ink acts as the tag's antenna and is applied to a paper substrate through conventional printing means. The silicon chip is attached to printed carbon-ink electrodes on the back of a paper label, creating a low-cost, disposable tag that can be integrated on the drug label. The information stored on the drug labels is written in a Medicine Markup Language (MML), which is based on the eXtensible Markup Language (XML). MML would allow all computers to communicate with any computer system in a similar way that Web servers read Hyper Text Markup Language (HTML), the common language used to create Web pages.

After receiving the medicine container, the patient places the medicine in a medicine cabinet, which is also equipped with a tag reader. This smart cabinet then tracks all medicine stored in it. It can track the medicine taken, how often the medicine is restocked and can let the patient know when a particular medication is about to expire. At this point, the server 200 can order these items automatically. The server 200 also monitors drug compliance, and if the patient does not remove the bottle to dispense medication as prescribed, the server 200 sends a warning to the healthcare provider.

The database tracks typical arm and leg movements to determine whether the user is experiencing muscle weakness reflective of a stroke. If muscle weakness is detected, the system presents the user with additional tests to confirm the likelihood of a stroke attack. If the information indicates a stroke had occurred, the system stores the time of the stroke detection and calls for emergency assistance to get timely treatment for the stroke. The user's habits and movements can be determined by the system for stroke detection. This is done by tracking location, ambulatory travel vectors and time in a database. If the user typically sleeps between 10 pm to 6 am, the location would reflect that the user's location maps to the bedroom between 10 pm and 6 am. In one exemplary system, the system builds a schedule of the user's activity as follows:

| Location | Time Start | Time End | Heart Rate |
|---|---|---|---|
| Bed room | 10 pm | 6 am | 60-80 |
| Gym room | 6 am | 7 am | 90-120 |
| Bath room | 7 am | 7:30 am | 85-120 |
| Dining room | 7:30 am | 8:45 am | 80-90 |
| Home Office | 8:45 am | 11:30 am | 85-100 |
| ... | | | |
| ... | | | |

Other data such as EKG can be tracked, for example. The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the user's ambulatory and living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j) (O(t)]$, where the $b(j) (O(t)$ term of the output symbol matrix is the probability of outputting observation $O(t)$, given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability $b(j) O(t)$ corresponds to the probability assigned by the model that the feature frame symbol is $O(t)$. The model arrangement is a matrix $A=[a(i,j)]$ of transition probabilities and a technique of computing $B=b(j) O(t)$, the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The system allows patients to conduct a low-cost, comprehensive, real-time monitoring of their vital parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

When used in conjunction with the Doppler radar, the wearable appliance is small, easily worn by the patient during periods of exercise or day-to-day activities, and non-invasively measures blood pressure can be done in a matter of seconds without affecting the patient. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's health condition. Certain cardiac conditions can be controlled, and in some cases predicted, before they actually occur. Moreover, data from the patient can be collected and analyzed while the patient participates in their normal, day-to-day activities.

Software programs associated with the Internet-accessible website, secondary software system, and the personal computer analyze the blood pressure, and heart rate, and pulse oximetry values to characterize the patient's cardiac condition. These programs, for example, may provide a report that features statistical analysis of these data to determine averages, data displayed in a graphical format, trends, and comparisons to doctor-recommended values.

When the appliance cannot communicate with the mesh network, the appliance simply stores information in memory and continues to make measurements. The watch component automatically transmits all the stored information (along with a time/date stamp) when it comes in proximity to the wireless mesh network, which then transmits the information through the wireless network.

In one embodiment, the server provides a web services that communicate with third party software through an interface. To generate vital parameters such as blood pressure information for the web services software interface, the patient continuously wears the blood-pressure monitor for a short period of time, e.g. one to two weeks after visiting a medical professional during a typical 'check up' or after signing up for a short-term monitoring program through the website. In this case, the wearable device such as the watch measures mobility through the accelerometer and blood pressure in a near-continuous, periodic manner such as every fifteen minutes. This information is then transmitted over the mesh network to a base station that communicates over the Internet to the server.

To view information sent from the blood-pressure monitor and fall detector on the wearable appliance, the patient or an authorized third party such as family members, emergency personnel, or medical professional accesses a patient user interface hosted on the web server 200 through the Internet 100 from a remote computer system. The patient interface displays vital information such as ambulation, blood pressure and related data measured from a single patient. The system may also include a call center, typically staffed with medical professionals such as doctors, nurses, or nurse practioners, whom access a care-provider interface hosted on the same website on the server 200. The care-provider interface displays vital data from multiple patients.

The wearable appliance has an indoor positioning system and processes these signals to determine a location (e.g., latitude, longitude, and altitude) of the monitor and, presumably, the patient. This location could be plotted on a map by the server, and used to locate a patient during an emergency, e.g. to dispatch an ambulance.

In one embodiment, the web page hosted by the server 200 includes a header field that lists general information about the patient (e.g. name, age, and ID number, general location, and information concerning recent measurements); a table that lists recently measured blood pressure data and suggested (i.e. doctor-recommended) values of these data; and graphs that plot the systolic and diastolic blood pressure data in a time-dependent manner. The header field additionally includes a series of tabs that each link to separate web pages that include, e.g., tables and graphs corresponding to a different data measured by the wearable device such as calorie consumption/dissipation, ambulation pattern, sleeping pattern, heart rate, pulse oximetry, and temperature. The table lists a series of data fields that show running average values of the patient's daily, monthly, and yearly vital parameters. The levels are compared to a series of corresponding 'suggested' values of vital parameters that are extracted from a database associated with the web site. The suggested values depend on, among other things, the patient's age, sex, and weight. The table then calculates the difference between the running average and suggested values to give the patient an idea of how their data compares to that of a healthy patient. The web software interface may also include security measures such as authentication, authorization, encryption, credential presentation, and digital signature resolution. The interface may also be modified to conform to industry-mandated, XML schema definitions, while being 'backwards compatible' with any existing XML schema definitions.

The system provides for self-registration of appliances by the user. Data can be synchronized between the Repository and appliance(s) via the base station 20. The user can preview the readings received from the appliance(s) and reject erroneous readings. The user or treating professional can set up the system to generate alerts against received data, based on pre-defined parameters. The system can determine trends in received data, based on user defined parameters.

Appliance registration is the process by which a patient monitoring appliance is associated with one or more users of the system. This mechanism is also used when provisioning appliances for a user by a third party, such as a clinician (or their respective delegate). In one implementation, the user (or delegate) logs into the portal to select one or more appliances and available for registration. In turn, the base station server 20 broadcasts a query to all nodes in the mesh network to retrieve identification information for the appliance such as manufacturer information, appliance model information, appliance serial number and optionally a hub number (available on hub packaging). The user may register more than one appliance at this point. The system optionally sets up a service subscription for appliance(s) usage. This includes selecting service plans and providing payment information. The appliance(s) are then associated with this user's account and a control file with appliance identification information is synchronized between the server 200 and the base station 20 and each appliance on initialization. In one embodiment, each appliance 8 transmits data to the base station 20 in an XML format for ease of interfacing and is either kept encrypted or in a non-readable format on the base station 20 for security reasons.

The base station 20 frequently collects and synchronizes data from the appliances 8. The base station 20 may use one of various transportation methods to connect to the repository on the server 200 using a PC as conduit or through a connection established using an embedded modem (connected to a phone line), a wireless router (DSL or cable wireless router), a cellular modem, or another network-connected appliance (such as, but not limited to, a web-phone, video-phone, embedded computer, PDA or handheld computer).

In one embodiment, users may set up alerts or reminders that are triggered when one or more reading meet a certain set of conditions, depending on parameters defined by the user. The user chooses the condition that they would like to be alerted to and by providing the parameters (e.g. threshold value for the reading) for alert generation. Each alert may have an interval which may be either the number of data points or a time duration in units such as hours, days, weeks or months. The user chooses the destination where the alert may be sent. This destination may include the user's portal, e-mail, pager, voice-mail or any combination of the above.

Trends are determined by applying mathematical and statistical rules (e.g. moving average and deviation) over a set of reading values. Each rule is configurable by parameters that are either automatically calculated or are set by the user.

The user may give permission to others as needed to read or edit their personal data or receive alerts. The user or clinician could have a list of people that they want to monitor and have it show on their "My Account" page, which serves as a local central monitoring station in one embodiment. Each person may be assigned different access rights which may be more or less than the access rights that the patient has. For example, a doctor or clinician could be allowed to edit data for example to annotate it, while the patient would have read-only privileges for certain pages.

An authorized person could set the reminders and alerts parameters with limited access to others. In one embodiment, the base station server 20 serves a web page customized by the user or the user's representative as the monitoring center that third parties such as family, physicians, or caregivers can log in and access information. In another embodiment, the base station 20 communicates with the server 200 at a call center so that the call center provides all services. In yet another embodiment, a hybrid solution where authorized representatives can log in to the base station server 20 access patient information while the call center logs into both the server 200 and the base station server 20 to provide complete care services to the patient.

The server 200 may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or a number of users via a summary "dashboard" of their readings data, with ability to drill-down into details for the collected data. A clinician administrator may monitor the data for and otherwise administer a number of users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about Patients that have been assigned to the Administrator by a Super Administrator. This allows for segmenting the entire population of monitored Patients amongst multiple Administrators. The Super Administrator may assign, remove and/or reassign Patients amongst a number of Administrators.

In one embodiment, a patient using an Internet-accessible computer and web browser, directs the browser to an appropriate URL and signs up for a service for a short-term (e.g., 1 month) period of time. The company providing the service completes an accompanying financial transaction (e.g. processes a credit card), registers the patient, and ships the patient a wearable appliance for the short period of time. The registration process involves recording the patient's name and contact information, a number associated with the monitor (e.g. a serial number), and setting up a personalized website. The patient then uses the monitor throughout the monitoring period, e.g. while working, sleeping, and exercising. During this time the monitor measures data from the patient and wirelessly transmits it through the channel to a data center. There, the data are analyzed using software running on computer servers to generate a statistical report. The computer servers then automatically send the report to the patient using email, regular mail, or a facsimile machine at different times during the monitoring period. When the monitoring period is expired, the patient ships the wearable appliance back to the monitoring company.

Different web pages may be designed and accessed depending on the end-user. As described above, individual users have access to web pages that only their ambulation and blood pressure data (i.e., the patient interface), while organizations that support a large number of patients (nursing homes or hospitals) have access to web pages that contain data from a group of patients using a care-provider interface. Other interfaces can also be used with the web site, such as interfaces used for: insurance companies, members of a particular company, clinical trials for pharmaceutical companies, and e-commerce purposes. Vital patient data displayed on these web pages, for example, can be sorted and analyzed depending on the patient's medical history, age, sex, medical condition, and geographic location. The web pages also support a wide range of algorithms that can be used to analyze data once they are extracted from the data packets. For example, an instant message or email can be sent out as an 'alert' in response to blood pressure indicating a medical condition that requires immediate attention. Alternatively, the message could be sent out when a data parameter (e.g. systolic blood pressure) exceeds a predetermined value. In some cases, multiple parameters (e.g., fall detection, positioning data, and blood pressure) can be analyzed simultaneously to generate an alert message. In general, an alert message can be sent out after analyzing one or more data parameters using any type of algorithm. These algorithms range from the relatively simple (e.g., comparing blood pressure to a recommended value) to the complex (e.g., predictive medical diagnoses using 'data mining' techniques). In some cases data may be 'fit' using algorithms such as a linear or non-linear least-squares fitting algorithm.

In one embodiment, a physician, other health care practitioner, or emergency personnel is provided with access to patient medical information through the server 200. In one embodiment, if the wearable appliance detects that the patient needs help, or if the patient decides help is needed, the system can call his or her primary care physician. If the patient is unable to access his or her primary care physician (or another practicing physician providing care to the patient) a call from the patient is received, by an answering service or a call center associated with the patient or with the practicing physician. The call center determines whether the patient is exhibiting symptoms of an emergency condition by polling vital patient information generated by the wearable device, and if so, the answering service contacts 911 emergency service or some other emergency service. The call center can review falls information, blood pressure information, and other vital information to determine if the patient is in need of emergency assistance. If it is determined that the patient in not exhibiting symptoms of an emergent condition, the answering service may then determine if the patient is exhibiting symptoms of a non-urgent condition. If the patient is exhibiting symptoms of a non-urgent condition, the answering service will inform the patient that he or she may log into the server 200 for immediate information on treatment of the condition. If the answering service determines that the patient is exhibiting symptoms that are not related to a non-urgent condition, the answering service may refer the patient to an emergency room, a clinic, the practicing physician (when the practicing physician is available) for treatment.

In another embodiment, the wearable appliance permits direct access to the call center when the user pushes a switch or button on the appliance, for instance. In one implementation, telephones and switching systems in call centers are integrated with the home mesh network to provide for, among other things, better routing of telephone calls, faster delivery of telephone calls and associated information, and improved service with regard to client satisfaction through computer-telephony integration (CTI). CTI implementations of various design and purpose are implemented both within individual call-centers and, in some cases, at the telephone network level. For example, processors running CTI software applications may be linked to telephone switches, service control points (SCPs), and network entry points within a public or private telephone network. At the call-center level, CTI-enhanced processors, data servers, transaction servers, and the like, are linked to telephone switches and, in some cases, to similar CTI hardware at the network level, often by a dedicated digital link. CTI processors and other hardware within a call-center is commonly referred to as customer premises equipment (CPE). It is the CTI processor and application software is such centers that provides computer enhancement to a call center. In a CTI-enhanced call center, telephones at agent stations are connected to a central telephony switching apparatus, such as an automatic call distributor (ACD) switch or a private branch exchange (PBX). The agent stations may also be equipped with computer terminals such as personal computer/video display unit's (PC/VDU's) so that agents manning such stations may have access to stored data as well as being linked to incoming callers by telephone equipment. Such stations may be interconnected through the PC/VDUs by a local area network (LAN). One or more data or transaction servers may also be connected to the LAN that interconnects agent stations. The LAN is, in turn, typically connected to the CTI processor, which is connected to the call switching apparatus of the call center.

When a call from a patient arrives at a call center, whether or not the call has been pre-processed at an SCP, the telephone number of the calling line and the medical record are made available to the receiving switch at the call center by the network provider. This service is available by most networks as caller-ID information in one of several formats such as Automatic Number Identification (ANI). Typically the number called is also available through a service such as Dialed Number Identification Service (DNIS). If the call center is computer-enhanced (CTI), the phone number of the calling party may be used as a key to access additional medical and/or historical information from a customer information system (CIS) database at a server on the network that connects the agent workstations. In this manner information pertinent to a call may be provided to an agent, often as a screen pop on the agent's PC/VDU.

The call center enables any of a first plurality of physician or health care practitioner terminals to be in audio communication over the network with any of a second plurality of patient wearable appliances. The call center will route the call to a physician or other health care practitioner at a physician or health care practitioner terminal and information related to the patient (such as an electronic medical record) will be received at the physician or health care practitioner terminal via the network. The information may be forwarded via a computer or database in the practicing physician's office or by a computer or database associated with the practicing physician, a health care management system or other health care facility or an insurance provider. The physician or health care practitioner is then permitted to assess the patient, to treat the patient accordingly, and to forward updated information related to the patient (such as examination, treatment and prescription details related to the patient's visit to the patient terminal) to the practicing physician via the network 200.

In one embodiment, the system informs a patient of a practicing physician of the availability of the web services and referring the patient to the web site upon agreement of the patient. A call from the patient is received at a call center. The call center enables physicians to be in audio communication over the network with any patient wearable appliances, and the call is routed to an available physician at one of the physician so that the available physician may carry on a two-way conversation with the patient. The available physician is permitted to make an assessment of the patient and to treat the patient. The system can forward information related to the patient to a health care management system associated with the physician. The health care management system may be a healthcare management organization, a point of service health care system, or a preferred provider organization. The health care practitioner may be a nurse practitioner or an internist.

The available health care practitioner can make an assessment of the patient and to conduct an examination of the patient over the network, including optionally by a visual study of the patient. The system can make an assessment in accordance with a protocol. The assessment can be made in accordance with a protocol stored in a database and/or making an assessment in accordance with the protocol may include displaying in real time a relevant segment of the protocol to the available physician. Similarly, permitting the physician to prescribe a treatment may include permitting the physician to refer the patient to a third party for treatment and/or referring the patient to a third party for treatment may include referring the patient to one or more of a primary care physician, specialist, hospital, emergency room, ambulance service or clinic. Referring the patient to a third party may additionally include communicating with the third party via an electronic link included in a relevant segment of a protocol stored in a protocol database resident on a digital storage medium and the electronic link may be a hypertext link. When a treatment is being prescribed by a physician, the system can communicate a prescription over the network to a pharmacy and/or communicating the prescription over the network to the pharmacy may include communicating to the pharmacy instructions to be given to the patient pertaining to the treatment of the patient. Communicating the prescription over the network to the pharmacy may also include communicating the prescription to the pharmacy via a hypertext link included in a relevant segment of a protocol stored in a database resident on a digital storage medium. In accordance with another related embodiment, permitting the physician to conduct the examination may be accomplished under conditions such that the examination is conducted without medical instruments at the patient terminal where the patient is located.

In another embodiment, a system for delivering medical examination, diagnosis, and treatment services from a physician to a patient over a network includes a first plurality of health care practitioners at a plurality of terminals, each of the first plurality of health care practitioner terminals including a display device that shows information collected by the wearable appliances and a second plurality of patient terminals or wearable appliances in audiovisual communication over a network with any of the first plurality of health care practitioner terminals. A call center is in communication with the patient wearable appliances and the health care practitioner terminals, the call center routing a call from a patient at one of the patient terminals to an available health care practitioner at one of the health care practitioner terminals, so that the available health care practitioner may carry on a two-way conversation with the patient. A protocol database resident on a digital storage medium is accessible to each of the health care practitioner terminals. The protocol database contains a plurality of protocol segments such that a relevant segment of the protocol may be displayed in real time on the display device of the health care practitioner terminal of the available health care practitioner for use by the available health care practitioner in making an assessment of the patient. The relevant segment of the protocol displayed in real time on the display device of the health care practitioner terminal may include an electronic link that establishes communication between the available health care practitioner and a third party and the third party may be one or more of a primary care physician, specialist, hospital, emergency room, ambulance service, clinic or pharmacy.

In accordance with other related embodiment, the patient wearable appliance may include establish a direct connection to the call center by pushing a button on the appliance. Further, the protocol database may be resident on a server that is in communication with each of the health care practitioner terminals and each of the health care practitioner terminals may include a local storage device and the protocol database is replicated on the local storage device of one or more of the physician terminals.

In another embodiment, a system for delivering medical examination, diagnosis, and treatment services from a physician to a patient over a network includes a first plurality of health care practitioner terminals, each of the first plurality of health care practitioner terminals including a display device and a second plurality of patient terminals in audio-visual communication over a network with any of the first plurality of health care practitioner terminals. Each of the second plurality of patient terminals includes a camera having pan, tilt and zoom modes, such modes being controlled from the first plurality of health care practitioner terminals. A call center is in communication with the patient terminals and the health care practitioner terminals and the call center routes a call from a patient at one of the patient terminals to an available health care practitioner at one of the health care practitioner terminals, so that the available health care practitioner may carry on a two-way conversation with the patient and visually observe the patient.

In one embodiment, the information is store in a secure environment, with security levels equal to those of online banking, social security number input, and other confidential information. Conforming to Health Insurance Portability and Accountability Act (HIPAA) requirements, the system creates audit trails, requires logins and passwords, and provides data encryption to ensure the patient information is private and secure. The HIPAA privacy regulations ensure a national floor of privacy protections for patients by limiting the ways that health plans, pharmacies, hospitals and other covered entities can use patients' personal medical information. The regulations protect medical records and other individually identifiable health information, whether it is on paper, in computers or communicated orally.

FIG. 2 shows an exemplary process to monitor patient. First the process sets up a wireless network with one transmitter and one receiver (1000). The process then determines chest movement using Doppler principle to infer vital signs such as heart activity (1002). The process then determines patient movement using the Doppler technique (1004). Sharp accelerations may be used to indicate fall. The system determines vital parameter including patient heart rate (1006). The system determines if patient needs assistance based on in-door position, fall detection and vital parameter (1008). If a fall is suspected, the system confirms the fall by communicating with the patient prior to calling a third party such as the patient's physician, nurse, family member, 911 call, 511 call, 411 call, or a paid call center to get assistance for the patient (1010). If confirmed or if the patient is non-responsive, the system contacts the third party and sends voice over mesh network to appliance on the patient to allow one or more third parties to talk with the patient (1012). If needed, the system calls and/or conferences emergency personnel into the call (1014).

FIG. 3 shows an exemplary network. Data collected and communicated on the display 1382 as well as voice is transmitted to a base station 1390 for communicating over a network to an authorized party 1394. The watch display 1382 and the base station is part of a mesh network that may communicate with a medicine cabinet to detect opening or to each medicine container 1391 to detect medication compliance. Other devices include mesh network thermometers, scales, or exercise devices. The mesh network also includes a plurality of home/room appliances 1392-1399. The ability to transmit voice is useful in the case the patient has fallen down and cannot walk to the base station 1390 to request help. Hence, in one embodiment, the watch captures voice from the user and transmits the voice over the Zigbee® mesh network to the base station 1390. The base station 1390 in turn dials out to an authorized third party to allow voice communication and at the same time transmits the collected patient vital parameter data and identifying information so that help can be dispatched quickly, efficiently and error-free. In one embodiment, the base station 1390 is a POTS telephone base station connected to the wired phone network. In a second embodiment, the base station 1390 can be a cellular telephone connected to a cellular network for voice and data transmission. In a third embodiment, the base station 1390 can be a WiMAX® or 802.16 standard base station that can communicate VoIP and data over a wide area network. In one implementation, Zigbee® or 802.15 appliances communicate locally and then transmits to the wide area network (WAN) such as the Internet over WiFi or WiMAX®. Alternatively, the base station can communicate with the WAN over POTS and a wireless network such as cellular or WiMAX® or both.

In one embodiment, the patient wears a garment fitted with piezoelectric devices that can generate power for a vital sign sensor such as an EKG sensor. The vibration energy harvester consists of three main parts. A piezoelectric transducer (PZT) serves as the energy conversion device, a specialized power converter rectifies the resulting voltage, and a capacitor or battery stores the power. The PZT takes the form of an aluminum cantilever with a piezoelectric patch. The vibration-induced strain in the PZT produces an ac voltage. The system repeatedly charges a battery or capacitor, which then operates the EKG/EMG sensors or other sensors at a relatively low duty cycle. In one embodiment, a vest made of piezoelectric materials can be wrapped around a person's chest to generate power when strained through breathing as breathing increases the circumference of the chest for an average human by about 2.5 to 5 cm. Energy can be constantly harvested because breathing is a constant activity, even when a person is sedate. The amount of energy captured through breathing indicates the breathing activity of the patient in addition to powering or charging the circuit. The energy is converted and stored in a low-leakage charge circuit until a predetermined threshold voltage is reached. Once the threshold is reached, the regulated power is allowed to flow for a sufficient period to power the wireless node such as the Zigbee® CPU/transceiver. The transmission is detected by nearby wireless nodes that are AC-powered and forwarded to the base station for signal processing. Power comes from the vibration of the system being monitored and the unit requires no maintenance, thus reducing life-cycle costs. In one embodiment, the housing of the unit can be PZT composite, thus reducing the weight.

In another embodiment, body energy generation systems include electro active polymers (EAPs) and dielectric elastomers. EAPs are a class of active materials that have a mechanical response to electrical stimulation and produce an electric potential in response to mechanical stimulation. EAPs are divided into two categories, electronic, driven by electric field, and ionic, driven by diffusion of ions. In one embodiment, ionic polymers are used as biological actuators that assist muscles for organs such as the heart and eyes. Since the ionic polymers require a solvent, the hydrated human body provides a natural environment. Polymers are actuated to contract, assisting the heart to pump, or correcting the shape of the eye to improve vision. Another use is as miniature surgical tools that can be inserted inside the body. EAPs can also be used as artificial smooth muscles, one of the original ideas for EAPs. These muscles could be placed in exoskeletal suits for soldiers or prosthetic devices for disabled persons. Along with the energy generation device, ionic polymers can be the energy storage vessel for harvesting energy. The capacitive characteristics of the EAP allow the polymers to be used in place of a standard capacitor bank. With EAP based jacket, when a person moves his/her arms, it will put the electro active material around the elbow in tension to generate power. Dielectric elastomers can support 50-100% area strain and generate power when compressed. Although the material could again be used in a bending arm type application, a shoe type electric generator can be deployed by placing the dielectric elastomers in the sole of a shoe. The constant compressive force provided by the feet while walking would ensure adequate power generation.

In another embodiment, the wireless node can be powered from thermal and/or kinetic energy. Temperature differentials between opposite segments of a conducting material result in heat flow and consequently charge flow since mobile, high-energy carriers diffuse from high to low concentration regions. Thermopiles consisting of n- and p-type materials electrically joined at the high-temperature junction are therefore constructed, allowing heat flow to carry the dominant charge carriers of each material to the low temperature end, establishing in the process a voltage difference across the base electrodes. The generated voltage and power is proportional to the temperature differential and the Seebeck coefficient of the thermoelectric materials. Body heat from a user's wrist is captured by a thermoelectric element whose output is boosted and used to charge the a lithium ion rechargeable battery. The unit utilizes the Seeback Effect which describes the voltage created when a temperature difference exists across two different metals. The thermoelectric generator takes body heat and dissipates it to the ambient air, creating electricity as well as sensing body temperature in the process.

In another embodiment, the kinetic energy of a person's movement is converted into energy. As a person moves their weight, a small weight inside the wireless node moves like a pendulum and turns a magnet to produce electricity which can be stored in a super-capacitor or a rechargeable lithium battery. Similarly, in a vibration energy embodiment, energy extraction from vibrations is based on the movement of a "spring-mounted" mass relative to its support frame. Mechanical acceleration is produced by vibrations that in turn cause the mass component to move and oscillate (kinetic energy). This relative displacement causes opposing frictional and damping forces to be exerted against the mass, thereby reducing and eventually extinguishing the oscillations. The damping forces literally absorb the kinetic energy of the initial vibration. This energy can be converted into electrical energy via an electric field (electrostatic), magnetic field (electromagnetic), or strain on a piezoelectric material. The kinetic energy can be used to measure the activity of the patient while providing energy or charging the circuits at the same time.

Another embodiment extracts energy from the surrounding environment using a small rectenna (microwave-power receivers or ultrasound power receivers) placed in patches or membranes on the skin or alternatively injected underneath the skin. The rectanna converts the received emitted power back to usable low frequency/dc power. A basic rectanna consists of an antenna, a low pass filter, an ac/dc converter and a dc bypass filter. The rectanna can capture renewable electromagnetic energy available in the radio frequency (RF) bands such as AM radio, FM radio, TV, very high frequency (VHF), ultra high frequency (UHF), global system for mobile communications (GSM), digital cellular systems (DCS) and especially the personal communication system (PCS) bands, and unlicensed ISM bands such as 2.4 GHz and 5.8 GHz bands, among others. The system captures the ubiquitous electromagnetic energy (ambient RF noise and signals) opportunistically present in the environment and transforming that energy into useful electrical power. The energy-harvesting antenna is preferably designed to be a wideband, omnidirectional antenna or antenna array that has maximum efficiency at selected bands of frequencies containing the highest energy levels. In a system with an array of antennas, each antenna in the array can be designed to have maximum efficiency at the same or different bands of frequency from one another. The collected RF energy is then converted into usable DC power using a diode-type or other suitable rectifier. This power may be used to drive, for example, an amplifier/filter module connected to a second antenna system that is optimized for a particular frequency and application. One antenna system can act as an energy harvester while the other antenna acts as a signal transmitter/receiver. The antenna circuit elements are formed using standard wafer manufacturing techniques. The antenna output is stepped up and rectified before presented to a trickle charger. The charger can recharge a complete battery by providing a larger potential difference between terminals and more power for charging during a period of time. If battery includes individual micro-battery cells, the trickle charger provides smaller amounts of power to each individual battery cell, with the charging proceeding on a cell by cell basis. Charging of the battery cells continues whenever ambient power is available. As the load depletes cells, depleted cells are switched out with charged cells. The rotation of depleted cells and charged cells continues as required. Energy is banked and managed on a micro-cell basis.

In one embodiment to monitor heart failure, the Doppler radar detects the presence or absence, or rate of change, or heart activity. A normal, healthy, heart beats at a regular rate. Irregular heart beats, known as cardiac arrhythmia, on the other hand, may characterize an unhealthy condition. Another unhealthy condition is known as congestive heart failure ("CHF"). CHF, also known as heart failure, is a condition where the heart has inadequate capacity to pump sufficient blood to meet metabolic demand. CHF may be caused by a variety of sources, including, coronary artery disease, myocardial infarction, high blood pressure, heart valve disease, cardiomyopathy, congenital heart disease, endocarditis, myocarditis, and others. Unhealthy heart conditions may be treated using a cardiac rhythm management (CRM) system. Examples of CRM systems, or pulse generator systems, include defibrillators (including implantable cardioverter defibrillator), pacemakers and other cardiac resynchronization devices.

The motion sensing capability of the Doppler radar can be used to provide reproducible measurements. Body activity will increase cardiac output and also change the amount of blood in the systemic venous system or lungs. Measurements of congestion may be most reproducible when body activity is at a minimum and the patient is at rest. The use of an accelerometer allows one to sense both body position and body activity. Comparative measurements over time may best be taken under reproducible conditions of body position and activity. Ideally, measurements for the upright position should be compared as among themselves. Likewise measurements in the supine, prone, left lateral decubitus and right lateral decubitus should be compared as among themselves. Other variables can be used to permit reproducible measurements, i.e. variations of the cardiac cycle and variations in the respiratory cycle. The ventricles are at their most compliant during diastole. The end of the diastolic period is marked by the QRS on the electrocardiographic means (EKG) for monitoring the cardiac cycle. The second variable is respiratory variation in impedance, which is used to monitor respiratory rate and volume. As the lungs fill with air during inspiration, impedance increases, and during expiration, impedance decreases. Impedance can be measured during expiration to minimize the effect of breathing on central systemic venous volume. While respiration and CHF both cause variations in impedance, the rates and magnitudes of the impedance variation are different enough to separate out the respiratory variations which have a frequency of about 8 to 60 cycles per minute and congestion changes which take at least several minutes to hours or even days to occur. Also, the magnitude of impedance change is likely to be much greater for congestive changes than for normal respiratory variation. Thus, the system can detect congestive heart failure (CHF) in early stages and alert a patient to prevent disabling and even lethal episodes of CHF. Early treatment can avert progression of the disorder to a dangerous stage.

Various physiological parameters of medical and research interest may be extracted from repetitive measurements of the areas of various cross-sections of the body. For example, pulmonary function parameters, such as respiration volumes and rates and apneas and their types, may be determined from measurements of, at least, a chest transverse cross-sectional area and also an abdominal transverse cross-sectional area. Cardiac parameters, such central venous pressure, left and right ventricular volumes waveforms, and aortic and carotid artery pressure waveforms, may be extracted from repetitive measurements of transverse cross-sectional areas of the neck and of the chest passing through the heart. From the cardiac-related signals, indications of ischemia may be obtained independently of any ECG changes. Ventricular wall ischemia is known to result in paradoxical wall motion during ventricular contraction (the ischemic segment paradoxically "balloons" outward instead of normally contracting inward). Such paradoxical wall motion, and thus indications of cardiac ischemia, may be extracted from chest transverse cross-section area measurements. Left or right ventricular ischemia may be distinguished where paradoxical motion is seen predominantly in left or right ventricular waveforms, respectively. For another example, observations of the onset of contraction in the left and right ventricles separately may be of use in providing feedback to bi-ventricular cardiac pacing devices. For a further example, pulse oximetry determines hemoglobin saturation by measuring the changing infrared optical properties of a finger. This signal may be disambiguated and combined with pulmonary data to yield improved information concerning lung function.

In one embodiment to monitor and predict stroke attack, a Doppler sensor is applied to detect fluids in the brain. The Doppler data is used to detect brain edema, which is defined as an increase in the water content of cerebral tissue which then leads to an increase in overall brain mass. Two types of brain edema are vasogenic or cytotoxic. Vasogenic edema is a result of increased capillary permeability. Cytotoxic edema reflects the increase of brain water due to an osmotic imbalance between plasma and the brain extracellular fluid. Cerebral edema in brain swelling contributes to the increase in intracranial pressure and an early detection leads to timely stroke intervention.

In yet another embodiment, a trans-cranial Doppler velocimetry sensor provides a non-invasive technique for measuring blood flow in the brain. An RF beam from a transducer is directed through the skull to produce a waveform of blood flow in the arteries using Doppler techniques. The data collected to determine the blood flow may include values such as the pulse cycle, blood flow velocity, end diastolic velocity, peak systolic velocity, mean flow velocity, total volume of cerebral blood flow, flow acceleration, the mean blood pressure in an artery, and the pulsatility index, or impedance to flow through a vessel. From this data, the condition of an artery may be derived, those conditions including stenosis, vasoconstriction, irreversible stenosis, vasodilation, compensatory vasodilation, hyperemic vasodilation, vascular failure, compliance, breakthrough, and pseudo-normalization.

In addition to the above techniques to detect stroke attack, the system can detect numbness or weakness of the face, arm or leg, especially on one side of the body. The system detects sudden confusion, trouble speaking or understanding, sudden trouble seeing in one or both eyes, sudden trouble walking, dizziness, loss of balance or coordination, or sudden, severe headache with no known cause.

In one embodiment to detect heart attack, the system detects discomfort in the center of the chest that lasts more than a few minutes, or that goes away and comes back. Symptoms can include pain or discomfort in one or both arms, the back, neck, jaw or stomach. The system can also monitor for shortness of breath which may occur with or without chest discomfort. Other signs may include breaking out in a cold sweat, nausea or lightheadedness.

In order to best analyze a patient's risk of stroke, additional patient data is utilized by a stroke risk analyzer. This data may include personal data, such as date of birth, ethnic group, sex, physical activity level, and address. The data may further include clinical data such as a visit identification, height, weight, date of visit, age, blood pressure, pulse rate, respiration rate, and so forth. The data may further include data collected from blood work, such as the anti-nuclear antibody panel, B-vitamin deficiency, C-reactive protein value, calcium level, cholesterol levels, entidal CO2, fibromogin, amount of folic acid, glucose level, hematocrit percentage, H-pylori antibodies, hemocysteine level, hypercapnia, magnesium level, methyl maloric acid level, platelets count, potassium level, sedrate (ESR), serum osmolality, sodium level, zinc level, and so forth. The data may further include the health history data of the patient, including alcohol intake, autoimmune diseases, caffeine intake, carbohydrate intake, carotid artery disease, coronary disease, diabetes, drug abuse, fainting, glaucoma, head injury, hypertension, lupus, medications, smoking, stroke, family history of stroke, surgery history, for example.

In one embodiment, data driven analyzers may be used to track the patient's risk of stroke or heart attack. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient stoke patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's EEG, EKG, BI, ultrasound, optical, acoustic, electromagnetic, or electrical parameters are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences. Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's stroke risks or heart attack risks. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the stroke or heart attack patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations O(1), O(2), . . . O(t), . . . , O(T), where each observation O(t) may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix A=[a(i,j)]. Each a(i,j) term of the transition matrix is the probability of making a transition to state j given that the model is in state i. The output symbol probability of the model is represented by a set of functions B=[b(j) (O(t)], where the b(j) (O(t) term of the output symbol matrix is the probability of outputting observation O(t), given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability b (j) O(t) corresponds to the probability assigned by the model that the feature frame symbol is O(t). The model arrangement is a matrix A=[a(i,j)] of transition probabilities and a technique of computing B=b(j) O(t), the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The automated analyzer can also consider related pathologies in analyzing a patient's risk of stroke, including but not limited to gastritis, increased intracranial pressure, sleep disorders, small vessel disease, and vasculitis.

In one embodiment, the processor and transceiver on the watch, the patch(es) and the base station conform to the Zigbee® protocol. Zigbee® is a cost-effective, standards-based wireless networking solution that supports low data-rates, low-power consumption, security, and reliability. Single chip Zigbee® controllers with wireless transceivers built-in include the Chipcon/Ember CC2420: Single-chip 802.15.4 radio transceiver and the FreeScale single chip Zigbee® and microcontroller. In various embodiments, the processor communicates with a Z axis accelerometer measures the patient's up and down motion and/or an X and Y axis accelerometer measures the patient's forward and side movements. In one embodiment, EKG and/or blood pressure parameters can be captured by the processor. The controllers upload the captured data when the memory is full or while in wireless contact with other Zigbee® nodes.

The wristwatch device can also be used to control home automation. The user can have flexible management of lighting, heating and cooling systems from anywhere in the home. The watch automates control of multiple home systems to improve conservation, convenience and safety. The watch can capture highly detailed electric, water and gas utility usage data and embed intelligence to optimize consumption of natural resources. The system is convenient in that it can be installed, upgraded and networked without wires. The patient can receive automatic notification upon detection of unusual events in his or her home. For example, if smoke or carbon monoxide detectors detect a problem, the wrist-watch can buzz or vibrate to alert the user and the central hub triggers selected lights to illuminate the safest exit route.

In another embodiment, the watch serves a key fob allowing the user to wirelessly unlock doors controlled by Zigbee® wireless receiver. In this embodiment, when the user is within range, the door Zigbee® transceiver receives a request to unlock the door, and the Zigbee® transceiver on the door transmits an authentication request using suitable security mechanism. Upon entry, the Zigbee® doorlock device sends access signals to the lighting, air-conditioning and entertainment systems, among others. The lights and temperature are automatically set to pre-programmed preferences when the user's presence is detected.

Although Zigbee® is mentioned as an exemplary protocol, other protocols such as UWB, Bluetooth®, WiFi and WiMAX® can be used as well.

While the foregoing addresses the needs of the elderly, the system can assist infants as well. Much attention has been given to ways to reduce a risk of dying from Sudden Infant Death Syndrome (SIDS), an affliction which threatens infants who have died in their sleep for heretofore unknown reasons. Many different explanations for this syndrome and ways to prevent the syndrome are found in the literature. It is thought that infants which sleep on their backs may be at risk of death because of the danger of formula regurgitation and liquid aspiration into the lungs. It has been thought that infants of six (6) months or less do not have the motor skills or body muscular development to regulate movements responsive to correcting breathing problems that may occur during sleep.

In an exemplary system to detect and minimize SIDS problem in an infant patient, a diaper pad is used to hold an array of integrated sensors and the pad can be placed over a diaper, clothing, or blanket. The integrated sensors can provide data for measuring position, temperature, sound, vibration, movement, and optionally other physical properties through additional sensors. Each pad can have sensors that provide one or more of the above data. The sensors can be added or removed as necessary depending on the type of data being collected.

The sensor can be water proof and disposable. The sensor can be switch on/off locally or remotely. The sensor can be removable or clip on easily. The sensor can store or beam out information for analysis purpose, e.g. store body temperature every 5 seconds. The sensor can be turn-on for other purposed, e.g. diaper wet, it will beep and allow a baby care provider to take care of the business in time. The array of sensors can be self selective, e.g., when one sensor can detect strong heart beat, it will turn off others to do so.

The sensor can be used for drug delivery system, e.g. when patient has abdomen pain, soothing drug can be applied, based on the level of pain the sensor detects, different dose of drugs will be applied.

The array of sensors may allow the selection and analysis of zones of sensors in the areas of interest such as the abdomen area. Each sensor array has a low spatial resolution: approximately 10 cm between each sensor. In addition to lower cost due to the low number of sensors, it is also possible to modify the data collection rate from certain sensors that are providing high-quality data. Other sensors may include those worn on the body, such as in watch bands, finger rings, or adhesive sensors, but telemetry, not wires, would be used to communicate with the controller.

The sensor can be passive device such as a reader, which mounted near the crib can active it from time to time. In any emergency situation, the sensor automatically signals a different state which the reader can detect.

The sensor can be active and powered by body motion or body heat. The sensor can detect low battery situation and warn the user to provide a replacement battery. In one embodiment, a plurality of sensors attached to the infant collects the vital parameters. For example, the sensors can be attached to the infant's clothing (shirt or pant), diaper, undergarment or bed sheet, bed linen, or bed spread.

The patient may wear one or more sensors, for example devices for sensing EMG, EKG, blood pressure, sugar level, weight, temperature and pressure, among others. In one embodiment, an optical temperature sensor can be used. In another embodiment, a temperature thermistor can be used to sense patient temperature. In another embodiment, a fat scale sensor can be used to detect the patient's fat content. In yet another embodiment, a pressure sensor such as a MEMS sensor can be used to sense pressure on the patient.

The CPU measures the time duration between the sequential pulses and converts each such measurement into a corresponding timing measurement indicative of heart rate. The CPU also processes a predetermined number of most recently occurring timing measurements in a prescribed fashion, to produce an estimate of heartbeat rate for display on a display device on the watch and/or for transmission over the wireless network. This estimate is updated with the occurrence of each successive pulse.

In one embodiment, the CPU produces the estimate of heartbeat rate by first averaging a plurality of measurements, then adjusting the particular one of the measurements that differs most from the average to be equal to that average, and finally computing an adjusted average based on the adjusted set of measurements. The process may repeat the foregoing operations a number of times so that the estimate of heartbeat rate is substantially unaffected by the occurrence of heartbeat artifacts.

The CPU measures the time durations between the successive pulses and estimates the heartbeat rate. The time durations between the successive pulses of the pulse sequence signal provides an estimate of heartbeat rate. Each time duration measurement is first converted to a corresponding rate, preferably expressed in beats per minute (bpm), and then stored in a file, taking the place of the earliest measurement previously stored. After a new measurement is entered into the file, the stored measurements are averaged, to produce an average rate measurement. The CPU optionally determines which of the stored measurements differs most from the average, and replaces that measurement with the average.

Upon initiation, the CPU increments a period timer used in measuring the time duration between successive pulses. This timer is incremented in steps of about two milliseconds in one embodiment. It is then determined whether or not a pulse has occurred during the previous two milliseconds. If it has not, the CPU returns to the initial step of incrementing the period timer. If a heartbeat has occurred, on the other hand, the CPU converts the time duration measurement currently stored in the period timer to a corresponding heartbeat rate, preferably expressed in bpm. After the heartbeat rate measurement is computed, the CPU determines whether or not the computed rate is intermediate prescribed thresholds of 20 bpm and 240 bpm. If it is not, it is assumed that the detected pulse was not in fact a heartbeat and the period timer is cleared.

Waveform averaging can be used to reduce noise. It reinforces the waveform of interest by minimizing the effect of any random noise. These pulses were obtained when the arm was motionless. If the arm was moved while capturing the data the waveform did not look nearly as clean. That's because motion of the arm causes the sonic vibrations to enter the piezo film through the arm or by way of the cable. An accelerometer is used to detect arm movement and used to remove inappropriate data capture.

In another embodiment, the automatic identification of the first, second, third and fourth heart sounds (S1, S2, S3, S4) is done. In yet another embodiment, based on the heart sound, the system analyzes the patient for mitral valve prolapse. The system performs a time-frequency analysis of an acoustic signal emanating from the subject's cardiovascular system and examines the energy content of the signal in one or more frequency bands, particularly higher frequency bands, in order to determine whether a subject suffers from mitral valve prolapse.

In one exemplary monitoring service providing system, such as an emergency service providing system, the system includes a communication network (e.g., the Public Switch Telephone Network or PSTN or POTS), a wide area communication network (e.g., TCP/IP network) in call centers. The communication network receives calls destined for one of the call centers. In this regard, each call destined for one of the call centers is preferably associated with a particular patient, a call identifier or a call identifier of a particular set of identifiers. A call identifier associated with an incoming call may be an identifier dialed or otherwise input by the caller. For example, the call centers may be locations for receiving calls from a particular hospital or nursing home.

To network may analyze the automatic number information (ANI) and/or automatic location information (ALI) associated with the call. In this regard, well known techniques exist for analyzing the ANI and ALI of an incoming call to identify the call as originating from a particular calling device or a particular calling area. Such techniques may be employed by the network to determine whether an incoming call originated from a calling device within an area serviced by the call centers. Moreover, if an incoming call originated from such an area and if the incoming call is associated with the particular call identifier referred to above, then the network preferably routes the call to a designated facility.

When a call is routed to the facility, a central data manager, which may be implemented in software, hardware, or a combination thereof, processes the call according to techniques that will be described in more detail hereafter and routes the call, over the wide area network, to one of the call centers depending on the ANI and/or ALI associated with the call. In processing the call, the central data manager may convert the call from one communication protocol to another communication protocol, such as voice over internet protocol (VoIP), for example, in order to increase the performance and/or efficiency of the system. The central data manager may also gather information to help the call centers in processing the call. There are various techniques that may be employed by the central data manager to enhance the performance and/or efficiency of the system, and examples of such techniques will be described in more detail hereafter.

Various benefits may be realized by utilizing a central facility to intercept or otherwise receive a call from the network and to then route the call to one of the call centers via WAN. For example, serving multiple call centers with a central data manager, may help to reduce total equipment costs. In this regard, it is not generally necessary to duplicate the processing performed by the central data manager at each of the call centers. Thus, equipment at each of the call centers may be reduced. As more call centers are added, the equipment savings enabled by implementing equipment at the central data manager instead of the call centers generally increases. Furthermore, the system is not dependent on any telephone company's switch for controlling the manner in which data is communicated to the call centers. In this regard, the central data manager may receive a call from the network and communicate the call to the destination call centers via any desirable communication technique, such as VoIP, for example. Data security is another possible benefit of the exemplary system 10 as the central data manager is able to store the data for different network providers associated with network on different partitions.

In one embodiment for professional users such as hospitals and nursing homes, a Central Monitoring Station provides alarm and vital sign oversight for a plurality of patients from a single computer workstation.

In one embodiment, software for the professional monitoring system provides a login screen to enter user name and password, together with database credentials. In Select Record function, the user can select a person, based on either entered or pre-selected criteria. From here navigate to their demographics, medical record, etc. The system can show a persons demographics, includes aliases, people involved in their care, friends and family, previous addresses, home and work locations, alternative numbers and custom fields. The system can show all data elements of a person's medical record. These data elements are not 'hard wired', but may be configured in the data dictionary to suit particular user requirements. It is possible to create views of the record that filter it to show (for instance) just the medications or diagnosis, etc. Any data element can be designated 'plan able' in the data dictionary and then scheduled. A Summary Report can be done. Example of a report displayed in simple format, selecting particular elements and dates. As many of these reports as required can be created, going across all data in the system based on some criteria, with a particular selection of fields and sorting, grouping and totaling criteria. Reports can be created that can format and analyze any data stored on the server. The system supports OLE controls and can include graphs, bar codes, etc. These can be previewed on screen, printed out or exported in a wide variety of formats. The system also maintains a directory of all organizations the administrator wishes to record as well as your own. These locations are then used to record the location for elements of the medical record (where applicable), work addresses for people involved in the care and for residential addresses for people in residential care. The data elements that form the medical record are not 'hard wired' (ie predefined) but may be customized by the users to suit current and future requirements.

More details on the system shown in FIG. 3 are discussed in co-pending U.S. application Ser. Nos. 11/768,381; 11/433,900 (May 12, 2006); Ser. No. 10/938,783 (Sep. 10, 2004); Ser. No. 11/252,279 (Oct. 16, 2005); Ser. No. 11/433, 282 (May 12, 2006); Ser. No. 11/439,631 (May 24, 2006); Ser. No. 11/480,206 (Jun. 30, 2006); Ser. No. 11/512,630 (Aug. 30, 2006); Ser. No. 11/480,231 (Jun. 30, 2006); and Ser. No. 11/588,197 (Oct. 24, 2006), the contents of which are incorporated by reference.

Figure 4A:
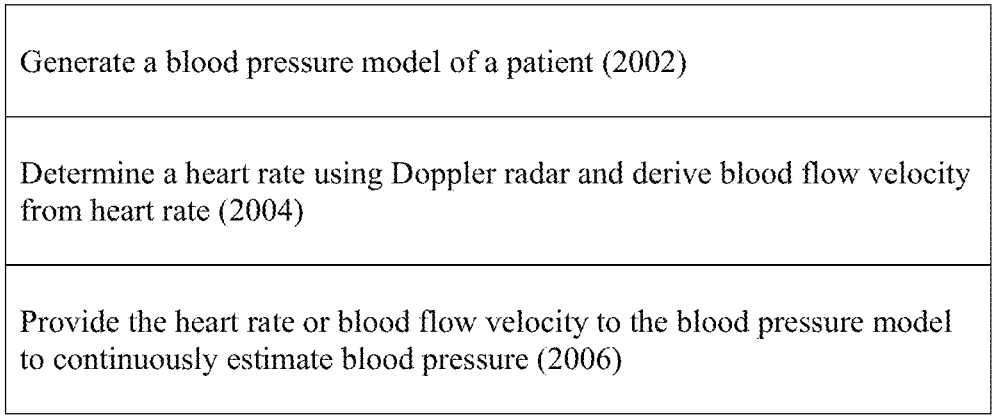
FIGS. 4A-4B show exemplary blood pressure determination processes.

FIG. 4A shows an exemplary process to continuously determine blood pressure of a patient. The process generates a blood pressure model of a patient (2002); determines a heart rate and/or blood flow velocity using a Doppler radar transducer (2004); and provides the heart rate and/or blood flow velocity to the blood pressure model to continuously estimate blood pressure (2006).

Figure 4B:
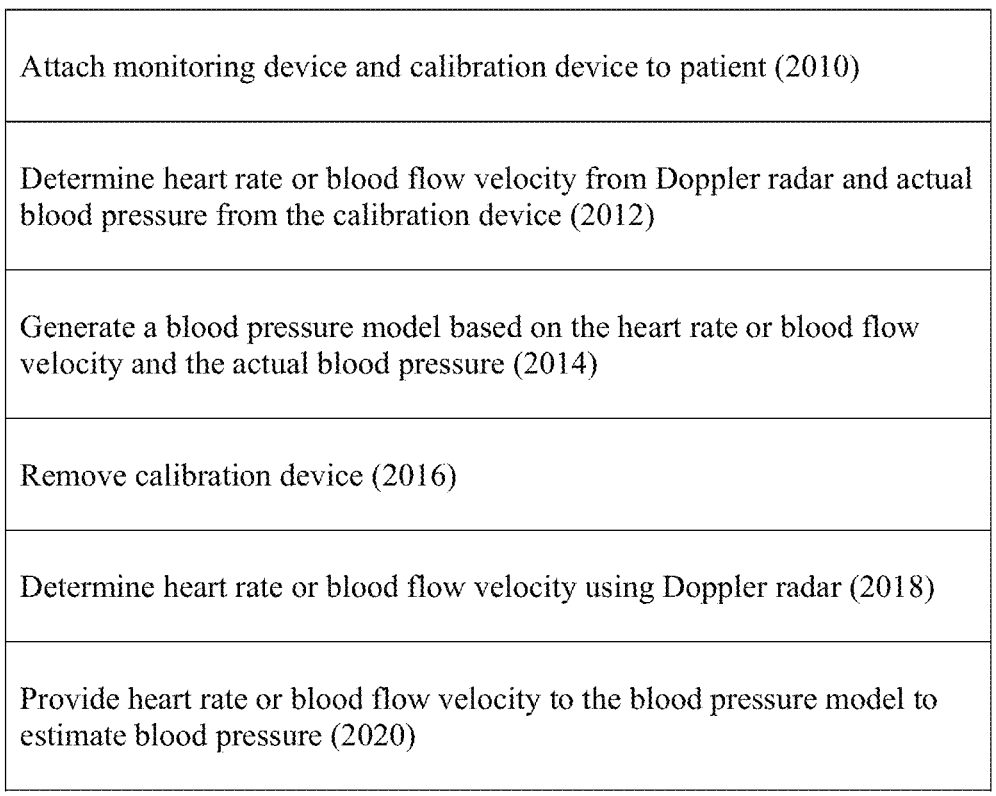

FIG. 4B shows another exemplary process to continuously determine blood pressure of a patient. First, during an initialization mode, a monitoring device and calibration device are attached to patient (2010). The monitoring device generates patient heart rate and/or blood flow velocity using Doppler radar, while actual blood pressure is measured by a calibration device (2012). Next, the process generates a blood pressure model based on the heart rate or blood flow velocity and the actual blood pressure (2014). Once this is done, the calibration device can be removed (2016). Next, during an operation mode, the process periodically samples heart rate or blood flow velocity from the monitoring device on a real-time basis (18) and provides the heart rate or blood flow velocity as input information to the blood pressure model to estimate blood pressure (20). This process can be done in continuously or periodically as specified by a user.

In one embodiment, to determine blood flow velocity, RF pulses are generated and transmitted into the artery. These pulses are reflected by various structures or entities within the artery (such as the artery walls, and the red blood cells within the subject's blood), and subsequently received as frequency shifts by the RF transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514,211, the content of which is incorporated by reference, discusses blood flow velocity using a time-frequency representation.

In one implementation, the system can obtain one or more numerical calibration curves describing the patient's vital signs such as blood pressure. The system can then direct energy such as RF energy (or alternatively infrared or ultrasound energy) at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and th SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart beats are denoised using six-stage wavelet decomposition, thresholding, and then reconstruction. Three feature extraction techniques were used: the Decimation method, and the wavelet method. Classification of the heart diseases is done using Hidden Markov Models (HMMs).

In yet another embodiment, a wavelet transform is applied to a window of two periods of heart sounds. Two analyses are realized for the signals in the window: segmentation of first and second heart sounds, and the extraction of the features. After segmentation, feature vectors are formed by using the wavelet detail coefficients at the sixth decomposition level. The best feature elements are analyzed by using dynamic programming.

In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

In one embodiment, the time intervals between the ECG R-waves are detected using an envelope detection process. The intervals between R and T waves are also determined. The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2. The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

In yet another embodiment, the S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A non linear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

In another embodiment, the first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifman 4th order wavelet kernel. The resulting vectors 4096 values, are reduced to 256 element feature vectors, this simplified the neural network and reduced noise.

In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

In another embodiment using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). The heart sound signals are processed to detect the first and second heart sounds in the following steps: a) wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

In one embodiment, heart sound is captured using a sound transducer located near the heart or near the carotid artery.

Once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

In one embodiment of the feature extractor, the digitized heart sound signal series s(n) is put through a low-order filter, typically a first-order finite impulse response filter, to spectrally flatten the signal and to make the signal less susceptible to finite precision effects encountered later in the signal processing. The signal is pre-emphasized preferably using a fixed pre-emphasis network, or preemphasizer. The signal can also be passed through a slowly adaptive pre-emphasizer. The preemphasized heart sound signal is next presented to a frame blocker to be blocked into frames of N samples with adjacent frames being separated by M samples. In one implementation, frame 1 contains the first 400 samples. The frame 2 also contains 400 samples, but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may also be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponds to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated, or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the preferred embodiment partitions the feature parameters into separate codebooks, preferably three. In the preferred embodiment, the first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound.

Dynamic programming obtains a relatively optimal time alignment between the heart sound to be recognized and the nodes of each word model, which compensates for the unavoidable differences in speaking rates which occur in different utterances of the same word. In addition, since dynamic programming scores words as a function of the fit between word models and the heart sound over many frames, it usually gives the correct word the best score, even if the word has been slightly misspoken or obscured by background sound. This is important, because humans often mispronounce words either by deleting or mispronouncing proper sounds, or by inserting sounds which do not belong.

In dynamic time warping (DTW), the input heart sound A, defined as the sampled time values $A=a(1) \ldots a(n)$, and the vocabulary candidate B, defined as the sampled time values $B=b(1) \ldots b(n)$, are matched up to minimize the discrepancy in each matched pair of samples. Computing the warping function can be viewed as the process of finding the minimum cost path from the beginning to the end of the words, where the cost is a function of the discrepancy between the corresponding points of the two words to be compared. Dynamic programming considers all possible points within the permitted domain for each value of i. Because the best path from the current point to the next point is independent of what happens beyond that point. Thus, the total cost of $[i(k), j(k)]$ is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the heart sound recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of heart sound against a given word model if the partial probability score for that comparison drops below a given threshold. This greatly reduces computation, since the dynamic programming of a given portion of heart sound against most words produces poor dynamic programming scores rather quickly, enabling most words to be pruned after only a small percent of their comparison has been performed. To reduce the computations involved, one embodiment limits the search to that within a legal path of the warping.

A Hidden Markov model can be used in one embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. The transitions between states are represented by a transition matrix $A=[a(i,j)]$. Each $a(i,j)$ term of the transition matrix is the probability of making a transition to state j given that the model is in state i. The output symbol probability of the model is represented by a set of functions B=[b(j)(O(t)], where the b(j)(O(t) term of the output symbol matrix is the probability of outputting observation O(t), given that the model is in state j. The first state is always constrained to be the initial state for the first time frame of the utterance, as only a prescribed set of left-to-right state transitions are possible. A predetermined final state is defined from which transitions to other states cannot occur. Transitions are restricted to reentry of a state or entry to one of the next two states. Such transitions are defined in the model as transition probabilities. For example, a heart sound pattern currently having a frame of feature signals in state 2 has a probability of reentering state 2 of a(2,2), a probability a(2,3) of entering state 3 and a probability of a(2,4)=1-a(2, 1)-a(2,2) of entering state 4. The probability a(2, 1) of entering state 1 or the probability a(2,5) of entering state 5 is zero and the sum of the probabilities a(2,1) through a(2,5) is one. Although the preferred embodiment restricts the flow graphs to the present state or to the next two states, one skilled in the art can build an HMM model without any transition restrictions.

The Markov model is formed for a reference pattern from a plurality of sequences of training patterns and the output symbol probabilities are multivariate Gaussian function probability densities. The heart sound traverses through the feature extractor. During learning, the resulting feature vector series is processed by a parameter estimator, whose output is provided to the hidden Markov model. The hidden Markov model is used to derive a set of reference pattern templates, each template representative of an identified S1-S4 pattern in a vocabulary set of reference patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

In one embodiment, a heart sound analyzer detects Normal S1, Split S1, Normal S2, Normal split S2, Wide split S2, Paradoxical split S2, Fixed split S2, S3 right ventricle origin, S3 left ventricle origin, opening snap, S4 right ventricle origin, S4 left ventricle origin, aortic ejection sound, and pulmonic ejection sound, among others. The sound analyzer can be an HMM type analyzer, a neural network type analyzer, a fuzzy logic type analyzer, a genetic algorithm type analyzer, a rule-based analyzer, or any suitable classifier. The heart sound data is captured, filtered, and the major features of the heart sound are determined and then operated by a classifier such as HMM or neural network, among others.

The analyzer can detect S1, whose major audible components are related to mitral and tricuspid valve closure. Mitral (MI) closure is the first audible component of the first sound. It normally occurs before tricuspid (T1) closure, and is of slightly higher intensity than T1. A split of the first sound occurs when both components that make up the sound are separately distinguishable. In a normally split first sound, the mitral and tricuspid components are 20 to 30 milliseconds apart. Under certain conditions a wide or abnormally split first sound can be heard. An abnormally wide split first sound can be due to either electrical or mechanical causes, which create asynchrony of the two ventricles. Some of the electrical causes may be right bundle branch block, premature ventricular beats and ventricular tachycardia. An apparently wide split can be caused by another sound around the time of the first. The closure of the aortic and pulmonic valves contributes to second sound production. In the normal sequence, the aortic valve closes before the pulmonic valve. The left sided mechanical events normally precede right sided events.

The system can analyze the second sound S2. The aortic (A2) component of the second sound is the loudest of the two components and is discernible at all auscultation sites, but especially well at the base. The pulmonic (P2) component of the second sound is the softer of the two components and is usually audible at base left. A physiological split occurs when both components of the second sound are separately distinguishable. Normally this split sound is heard on inspiration and becomes single on expiration. The A2 and P2 components of the physiological split usually coincide, or are less than 30 milliseconds apart during expiration and often moved to around 50 to 60 milliseconds apart by the end of inspiration. The physiological split is heard during inspiration because it is during that respiratory cycle that intrathoracic pressure drops. This drop permits more blood to return to the right heart. The increased blood volume in the right ventricle results in a delayed pulmonic valve closure. At the same time, the capacity of the pulmonary vessels in the lung is increased, which results in a slight decrease in the blood volume returning to the left heart. With less blood in the left ventricle, its ejection takes less time, resulting in earlier closing of the aortic valve. Therefore, the net effect of inspiration is to cause aortic closure to occur earlier, and pulmonary closure to occur later. Thus, a split second is heard during inspiration, and a single second sound is heard during expiration. A reversed (paradoxical) split of the second sound occurs when there is a reversal of the normal closure sequence with pulmonic closure occurring before aortic. During inspiration the second sound is single, and during expiration the second sound splits. This paradoxical splitting of the second sound may be heard when aortic closure is delayed, as in marked volume or pressure loads on the left ventricle (i.e., aortic stenosis) or with conduction defects which delay left ventricular depolarization (i.e., left bundle branch block). The normal physiological split second sound can be accentuated by conditions that cause an abnormal delay in pulmonic valve-1 closure. Such a delay may be due to an increased volume in the right ventricle as o compared with the left (atrial septal defect, or ventricular septal defect); chronic right ventricular outflow obstruction (pulmonic stenosis); acute or chronic dilatation of the. right ventricle due to sudden rise in pulmonary artery pressure (pulmonary embolism); electrical delay or activation of AA the right ventricle (right bundle branch block); decreased elastic recoil of the pulmonary artery (idiopathic dilatation of the pulmonary artery). The wide split has a duration of 40 to 50' milliseconds, compared to the normal physiologic split of 30 milliseconds. Fixed splitting of the second sound refers to split sound which displays little or no respiratory variation. The two components making up the sound occur in their normal sequence, but the ventricles are unable to change their volumes with respiration. This finding is typical in atrial septal defect, but is occasionally heard in congestive heart failure. The fixed split is heard best at base left with the diaphragm.

The third heart sound is also of low frequency, but it is heard just after the second heart sound. It occurs in early diastole, during the time of rapid ventricular filling. This sound occurs about 140 to 160 milliseconds after the second sound. The S3 is often heard in normal children or young adults but when heard in individuals over the age of 40 it usually reflects cardiac disease characterized by ventricular dilatation, decreased systolic function, and elevated ventricular diastolic filling pressure. The nomenclature includes the term ventricular gallop, protodiastolic gallop, S3 gallop, or the more common, S3. When normal it is referred to as a physiological third heart sound, and is usually not heard past the age of forty. The abnormal, or pathological third heart sound, may be heard in individuals with coronary artery disease, cardiomyopathies, incompetent valves, left to right shunts, Ventricular Septal Defect (VSD), or Patent Ductus Arteriosus (PDA). The pathological S3 may be the first clinical sign of congestive heart failure. The fourth heart sound is a low frequency sound heard just before the first heart sound, usually preceding this sound by a longer interval than that separating the two components of the normal first sound. It has also been known as an "atrial gallop", a "presystolic gallop", and an "S4 gallop". It is most commonly known as an "S4".

The S4 is a diastolic sound, which occurs during the late diastolic filling phase at the time when the atria contract. When the ventricles have a decreased compliance, or are receiving an increased diastolic volume, they generate a low frequency vibration, the S4. Some authorities believe the S4 may be normal in youth, but is seldom considered normal after the age of 20. The abnormal or pathological S4 is heard in primary myocardial disease, coronary artery disease, hypertension, and aortic and pulmonic stenosis. The S4 may have its origin in either the left or right heart. The S4 of left ventricular origin is best heard at the apex, with the patient supine, or in the left lateral recumbent position. Its causes include severe hypertension, aortic stenosis, cardiomyopathies, and left ventricular myocardial infarctions. In association with ischemic heart disease the S4 is often loudest during episodes of angina pectoris or may occur early after an acute myocardial infarction, often becoming fainter as the patient improves. The S4 of right ventricular origin is best heard at the left lateral sternal border. It is usually accentuated with inspiration, and may be due to pulmonary stenosis, pulmonary hypertension, or right ventricular myocardial infarction. When both the third heart sound and a fourth heart sound are present, with a normal heart rate, 60-100 heart beats per minute, the four sound cadence of a quadruple rhythm may be heard.

Ejection sounds are high frequency clicky sounds occurring shortly after the first sound with the onset of ventricular ejection. They are produced by the opening of the semilunar valves, aortic or pulmonic, either when one of these valves is diseased, or when ejection is rapid through a normal valve. They are heard best at the base, and may be of either aortic or pulmonic origin. Ejection sounds of aortic origin often radiate widely and may be heard anywhere on a straight line from the base right to the apex. Aortic ejection sounds are most typically heard in patients with valvular aortic stenosis, but are occasionally heard in various other conditions, such as aortic insufficiency, coarctation of the aorta, or aneurysm of the ascending aorta. Ejection sounds of pulmonic origin are heard anywhere on a straight line from base left, where they are usually best heard, to the epigastrium. Pulmonic ejection sounds are typically heard in pulmonic stenosis, but may be encountered in pulmonary hypertension, atrial septal defects (ASD) or in conditions causing enlargement of the pulmonary artery. Clicks are high frequency sounds which occur in systole, either mid, early, or late. The click generally occurs at least 100 milliseconds after the first sound. The most common cause of the click is mitral valve prolapse. The clicks of mitral origin are best heard at the apex, or toward the left lateral sternal border. The click will move closer to the first sound when volume to the ventricle is reduced, as occurs in standing or the Valsalva maneuver. The opening snap is a short high frequency sound, which occurs after the second heart sound in early diastole. It usually follows the second sound by about 60 to 100 milliseconds. It is most frequently the result of the sudden arrest of the opening of the mitral valve, occurring in mitral stenosis, but may also be encountered in conditions producing increased flow through this valve (i.e., VSD or PDA). In tricuspid stenosis or in association with increased flow across the tricuspid valve, as in ASD, a tricuspid opening snap may be heard. The tricuspid opening snap is loudest at the left lateral sternal border, and becomes louder with inspiration.

Murmurs are sustained noises that are audible during the time periods of systole, diastole, or both. They are basically produced by these factors: 1) Backward regurgitation through a leaking valve or septal defect; 2) Forward flow through a narrowed or deformed valve or conduit or through an arterial venous connection; 3) High rate of blood flow through a normal or abnormal valve; 4) Vibration of loose structures within the heart (i.e., chordae tendineae or valvular tissue). Murmurs that occur when the ventricles are contracting, that is, during systole, are referred to as systolic murmurs. Murmurs occurring when the ventricles are relaxed and filling, that is during diastole, are referred to as diastolic murmurs. There are six characteristics useful in murmur identification and differentiation:

1) Location or the valve area over which the murmur is best heard. This is one clue to the origin of the murmur. Murmurs of mitral origin are usually best heard at the apex. Tricuspid murmurs at the lower left lateral sternal border, and pulmonic murmurs at base left. Aortic systolic murmurs are best heard at base right, and aortic diastolic murmurs at Erb's point, the third intercostal space to the left of the sternum.
2) Frequency (pitch). Low, medium, or high.
3) Intensity.
4) Quality.
5) Timing. (Occurring during systole, diastole, or both).
6) Areas where the sound is audible in addition to the area over which it is heard best.

Systolic murmurs are sustained noises that are audible during the time period of systole, or the period between S1 and S2. Forward flow across the aortic or pulmonic valves, or regurgitant flow from the mitral or tricuspid valve may produce a systolic murmur. Systolic murmurs may be normal, and can represent normal blood flow, i.e., thin chest, babies and children, or increased blood flow, i.e., pregnant women. Early systolic murmurs begin with or shortly after the first sound and peak in the first third of systole. Early murmurs have the greatest intensity in the early part of the cycle. The commonest cause is the innocent murmur of childhood (to be discussed later). A small ventricular septal defect (VSD) occasionally causes an early systolic murmur. The early systolic murmur of a small VSD begins with S1 and stops in mid systole, because as ejection continues and the ventricular size decreases, the small defect is sealed shut, causing the murmur to soften or cease. This murmur is characteristic of the type of children's VSD located in the muscular portion of the ventricular septum. This defect may disappear with age. A mid-systolic murmur begins shortly after the first sound, peaks in the middle of systole, and does not quite extend to the second sound. It is the crescendo decrescendo murmur which builds up and decrease symmetrically. It is also known as an ejection murmur. It most commonly is due to forward blood flow through a normal, narrow or irregular valve, i.e., aortic or pulmonic stenosis. The murmur begins when the pressure in the respective ventricle exceeds the aortic or pulmonary arterial pressure. The most characteristic feature of this murmur is its cessation before the second sound, thus leaving this latter sound identifiable as a discrete entity. This type of murmur is commonly heard in normal individuals, particularly in the young, who usually have increased blood volumes flowing over normal valves. In this setting the murmur is usually short, with its peak intensity early in systole, and is soft, seldom over 2 over 6 in intensity. It is then designated as an innocent murmur. In order for a murmur to be classified as innocent (i.e. normal), the following are present:
1) Normal splitting of the second sound together with absence of abnormal sounds or murmurs, such as ejection sounds, diastolic murmurs, etc.
2) Normal jugular venus and carotid pulses
3) Normal precordial pulsations or palpation, and
4) Normal chest x-ray and ECG Obstruction or stenosis across the aortic or pulmonic valves also may give rise to a murmur of this type. These murmurs are usually longer and louder than the innocent murmur, and reach a peak intensity in mid-systole. The murmur of aortic stenosis is harsh in quality and is heard equally well with either the bell or the diaphragm. It is heard best at base right, and radiates to the apex and to the neck bilaterally.

An early diastolic murmur begins with a second sound, and peaks in the first third of diastole. Common causes are aortic regurgitation and pulmonic regurgitation. The early diastolic murmur of aortic regurgitation usually has a high frequency blowing quality, is heard best with a diaphragm at Erb's point, and radiates downward along the left sternal border. Aortic regurgitation tends to be of short duration, and heard best on inspiration. This respiratory variation is helpful in differentiating pulmonic regurgitation from aortic regurgitation. A mid-diastolic murmur begins after the second sound and peaks in mid-diastole. Common causes are mitral stenosis, and tricuspid stenosis. The murmur of mitral stenosis is a low frequency, crescendo de crescendo rumble, heard at the apex with the bell lightly held. If it radiates, it does so minimally to the axilla. Mitral stenosis normally produces three distinct abnormalities which can be heard: 1) A loud first sound 2) An opening snap, and 3) A mid-diastolic rumble with a late diastolic accentuation. A late diastolic murmur occurs in the latter half of diastole, synchronous with atrial contraction, and extends to the first sound. Although occasionally occurring alone, it is usually a component of the longer diastolic murmur of mitral stenosis or tricuspid stenosis. This murmur is low in frequency, and rumbling in quality. A continuous murmur usually begins during systole and extends through the second sound and throughout the diastolic period. It is usually produced as a result of one of four mechanisms: 1) An abnormal communication between an artery and vein; 2) An abnormal communication between the aorta and the right side of the heart or with the left atrium; 3) An abnormal increase in flow, or constriction in an artery; and 4) Increased or turbulent blood flow through veins. Patent Ductus Arteriosus (PDA) is the classical example of this murmur. This condition is usually corrected in childhood. It is heard best at base left, and is usually easily audible with the bell or diaphragm. Another example of a continuous murmur is the so-called venous hum, but in this instance one hears a constant roaring sound which changes little with the cardiac cycle. A late systolic murmur begins in the latter half of systole, peaks in the later third of systole, and extends to the second sound. It is a modified regurgitant murmur with a backward flow through an incompetent valve, usually the mitral valve. It is commonly heard in mitral valve prolapse, and is usually high in frequency (blowing in quality), and heard best with a diaphragm at the apex. It may radiate to the axilla or left sternal border. A pansystolic or holosystolic murmur is heard continuously throughout systole. It begins with the first heart sound, and ends with the second heart sound. It is commonly heard in mitral regurgitation, tricuspid regurgitation, and ventricular septal defect. This type of murmur is caused by backward blood flow. Since the pressure remains higher throughout systole in the ejecting chamber than in the receiving chamber, the murmur is continuous throughout systole. Diastolic murmurs are sustained noises that are audible between S2 and the next S. Unlike systolic murmurs, diastolic murmurs should usually be considered pathological, and not normal. Typical abnormalities causing diastolic murmurs are aortic regurgitation, pulmonic regurgitation, mitral stenosis, and tricuspid stenosis. The timing of diastolic murmurs is the primary concern of this program. These murmurs can be early, mid, late and pan in nature. In a pericardial friction rub, there are three sounds, one systolic, and two diastolic. The systolic sound may occur anywhere in systole, and the two diastolic sounds occur at the times the ventricles are stretched. This stretching occurs in early diastole, and at the end of diastole. The pericardial friction rub has a scratching, grating, or squeaking leathery quality. It tends to be high in frequency and best heard with a diaphragm. A pericardial friction rub is a sign of pericardial inflammation and may be heard in infective pericarditis, in myocardial infarction, following cardiac surgery, trauma, and in autoimmune problems such as rheumatic fever.

In addition to heart sound analysis, the timing between the onset and offset of particular features of the ECG (referred to as an interval) provides a measure of the state of the heart and can indicate the presence of certain cardiological conditions.

In addition to providing beat-to-beat timing information for other sensors to use, the patterns of the constituent waveform features determined by the HMM or neural networks, among other classifiers, can be used for detecting heart attacks or stroke attacks, among others. For example, the detection and classification of ventricular complexes from the ECG data is can be used for rhythm and various types of arrhythmia to be recognized. The system analyzes pattern recognition parameters for classification of normal QRS complexes and premature ventricular contractions (PVC). Exemplary parameters include the width of the QRS complex, vectorcardiogram parameters, amplitudes of positive and negative peaks, area of positive and negative waves, various time-interval durations, amplitude and angle of the QRS vector, among others. The EKG analyzer can analyze EKG/ECG patterns for Hypertrophy, Enlargement of the Heart, Atrial Enlargement, Ventricular Hypertrophy, Arrhythmias, Ectopic Supraventricular Arrhythmias, Ventricular Tachycardia (VT), Paroxysmal Supraventricular Tachycardia (PSVT), Conduction Blocks, AV Block, Bundle Branch Block, Hemiblocks, Bifascicular Block, Preexcitation Syndromes, Wolff-Parkinson-White Syndrome, Lown-Ganong-Levine Syndrome, Myocardial Ischemia, Infarction, Non-Q Wave Myocardial Infarction, Angina, Electrolyte Disturbances, Heart Attack, Stroke Attack, Hypothermia, Pulmonary Disorder, Central Nervous System Disease, or Athlete's Heart, for example.

FIG. 4C shows an exemplary process to detect stroke attack. In this embodiment, 3D accelerometer sensing is used. First, the process looks for weakness (hemiparesis) in either the left half or the right half of the body, for example the left/right arms, legs, or face (3000). Next, the system analyzes walking pattern to see if the patient has a loss of balance or coordination (3002). The system then asks the user to move hands/feet in a predetermined pattern (3004) and reads accelerometer output in accordance with predetermined pattern movement (3006). For example, the system can ask the user to point his/her right or left hand to the nose. The accelerometer outputs are tested to check if the correct hand did reach the nose. In another example, the user can be prompted to extend his or her hands on both side and wiggle the hands or to kick the legs. Again, the outputs of the accelerometers are used to confirm that the user is able to follow direction. The accelerometer outputs are provided to a pattern classifier, which can be an HMM, a neural network, a Bayesian network, fuzzy logic, or any suitable classifiers (3008). The system also checks whether patient is experiencing dizziness or sudden, severe headache with no known cause (3010). Next, the system displays a text image and asks the patient to read back the text image, one eye at a time (3012). Using a speech recognizer module, the user speech is converted into text to compare against the text image. The speech recognizer also detects if the user exhibits signs of confusion, trouble speaking or understanding (3014). The system also asks the patient if they feel numbness in the body-arms, legs, face (3016). Next the system asks the patient to squeeze gauge/force sensor to determine force applied during squeeze (3018). If any of the above tests indicate a possible stroke, the system displays a warning to the patient and also connects the patient to the appropriate emergency response authority, family member, or physician.

Figure 4D:
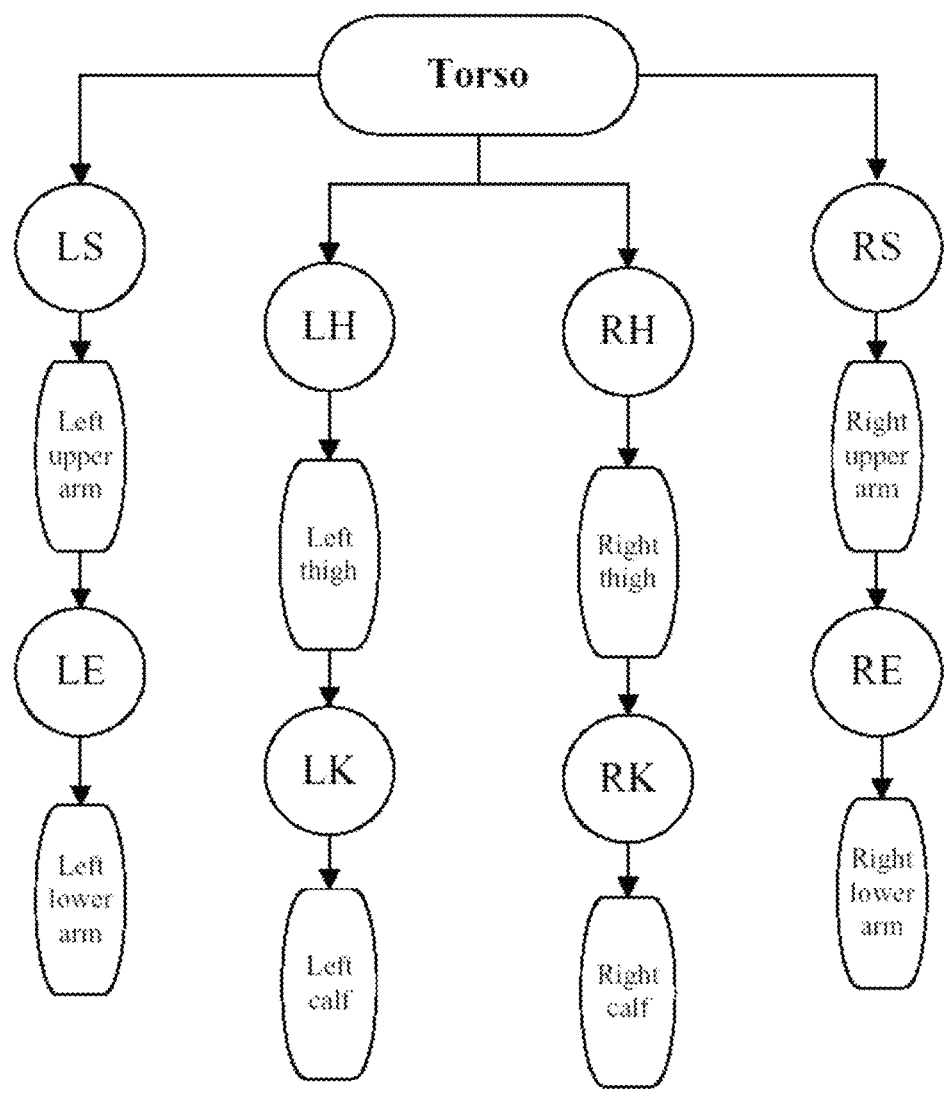

In one implementation, an HMM is used to track patient motor skills or patient movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee® wireless sensors with tri-axial accelerometers are mounted to the patient on different body locations for recording, for example the tree structure as shown in FIG. 4D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generates a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the patient through additional tests to confirm a stroke attack, and if a stroke attack is suspected, the system prompts the user to seek medical attention immediately and preferably within the 3 hour for receiving TPA.

FIG. 4E shows one exemplary process for determining weakness in the left or right half of the body. The process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the patient to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

The system can detect hemiparesis, a very common symptom of stroke, by detecting muscular weakness or partial paralysis to one side of the body. Additionally, the accelerometers can detect ataxia, which is an impaired ability to perform smooth coordinated voluntary movements. Additionally, the system can detect aphasia, including receptive aphasia and expressive aphasia. Aphasia is a cognitive disorder marked by an impaired ability to comprehend (receptive aphasia) or express (expressive aphasia) language. Exemplary embodiments are disclosed for detecting receptive aphasia by displaying text or playing verbal instructions to the user, followed by measuring the correctness and/or time delay of the response from the user. Exemplary embodiments are also disclosed for detecting expressive aphasia by positing sound made by an animal to the user, prompting the user to identify or name the animal, and measuring the correctness and/or time delay of the response from the user. The system can also detect dysarthria, a disorder of speech articulation (e.g., slurred speech), by prompting the user to say a word or phrase that is recorded for subsequent comparison by voice pattern recognition or evaluation by medical personnel.

In the above manner, the system automatically reminds the user to get help if he feels a sudden numbness or weakness of the face, arm or leg, especially on one side of the body, sudden confusion, trouble speaking or understanding, sudden trouble seeing in one or both eyes, or sudden trouble walking, dizziness, loss of balance or coordination.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a job lifting boxes, among others. In one alternative embodiment, angular position sensors, one on each side of the hip joint, can be used to distinguish lying down, sitting, and standing positions. In another embodiment, the present invention repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

Depending on the severity of the stroke, patients can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Patients with pure motor hemiparesis present with face, arm, and leg weakness. This condition usually affects the extremities equally, but in some cases it affects one extremity more than the other. The most common stroke location in affected patients is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Patients with clumsy-hand dysarthria syndrome experience unilateral hand weakness and dysarthria. The dysarthria is often severe, whereas the hand involvement is more subtle, and patients may describe their hand movements as "awkward." This syndrome is usually caused by an infarct in the pons.

Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)-suggest hemispheric dysfunction with involvement of a superficial territory from an atherothrombotic or embolic occlusion of a mainstem vessel or peripheral branch.

The system can detect a pattern of motor weakness. Ischemia of the cortex supplied by the middle cerebral artery typically causes weakness that (1) is more prominent in the arm than in the leg and (2) involves the distal muscles more than the proximal muscles. Conversely, involvement of an area supplied by the superficial anterior cerebral artery results in weakness that (1) is more prominent in the leg than the arm and (2) involves proximal upper extremity (shoulder) muscles more than distal upper extremity muscles. Flaccid paralysis of both the arm and leg (unilateral) suggests ischemia of the descending motor tracts in the basal ganglia or brainstem. This is often caused by an occlusion of a penetrating artery as a result of small-vessel disease. Once the stroke is detected, intravenous (IV) tissue plasminogen activator (t-PA) needs to be given within 3 hours of symptom onset. An accurate assessment of the timing of the stroke is also crucial. The system keeps track of the timing off the onset of the stroke for this purpose.

In yet a further embodiment for performing motor motion analysis, an HMM is used to determine the physical activities of a patient, to monitor overall activity levels and assess compliance with a prescribed exercise regimen and/or efficacy of a treatment program. The HMM may also measure the quality of movement of the monitored activities. For example, the system may be calibrated or trained in the manner previously described, to recognize movements of a prescribed exercise program. Motor function information associated with the recognized movements may be sent to the server for subsequent review. A physician, clinician, or physical therapist with access to patient data may remotely monitor compliance with the prescribed program or a standardized test on motor skill. For example, patients can take the Wolf Motor Function test and acceleration data is captured on the following tasks:

placing the forearm on a table from the side
moving the forearm from the table to a box on the table from the side
extending the elbow to the side
extending the elbow to the side against a light weight
placing the hand on a table from the front
moving the hand from table to box
flexing the elbow to retrieve a light weight
lifting a can of water
lifting a pencil, lifting a paper clip
stacking checkers, flipping cards
turning a key in a lock
folding a towel
lifting a basket from the table to a shelf above the table.

The above system can be implemented using a person computer or can be implemented on a game machine such as Nintendo's Wii. The Wii controller has the ability to sense its position in three-dimensional space in relation to the television set. After placing sensors next to the television, players will have the ability to hold the controller (or freehand as many call it) with one hand in the same way they would a television remote. The three known input methods the freehand allows are:

Standard button input, such as pressing the "A" button or D-pad to execute a move.

Three dimensional input, which gives players the ability to move or rotate the freehand controller in different directions on any axis.

Pointer functionality, which turns the controller into a mouse of sorts, with the ability to move a cursor around on screen.

The Wii controller—called the Wii Remote by Nintendo, dubbed the Wiimote by fans—also connects to several peripherals at the end of the controller. A built-in speaker system can be placed in the middle of the controller, allowing players to hear sounds not only from the televisions but transferred directly to the controller.

"Computer readable media" can be any available media that can be accessed by client/server devices. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by client/server devices. Communication media typically embodies computer readable instructions, data structures, program modules or other data in a modulated data signal such as a carrier wave or other transport mechanism and includes any information delivery media.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only. The above specification, examples and data provide a complete description of the manufacture and use of the composition of the invention. Since many embodiments of the invention can be made without departing from the spirit and scope of the invention, the invention resides in the claims hereinafter appended.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A monitoring system, comprising:
a Doppler radar formed with an IEEE 802 protocol transmitter and an IEEE 802 protocol receiver to detect body motion of a person, wherein frequency waves are transmitted by the IEEE 802 protocol transmitter and reflected waves are received by the IEEE 802 protocol receiver as part of a multiple input, multiple output (MIMO) wireless adapter chip set coupled to a plurality of antennas and a plurality of radios which send data over two transceivers simultaneously, wherein the Doppler radar is configured to generate an operational Doppler radar signal; and
an analyzer configured to perform Doppler operations using the IEEE 802 protocol transmitter and receiver, wherein the analyzer calibrates a training Doppler radar signal with a training body position during a training phase to develop a model and wherein the analyzer is configured to use the model with the operational Doppler radar signal during an operational phase to determine a body position of the person.

2. The system of claim 1, further comprising non-transitory computer medium configured to identify one person from another based on heart rate signature characteristics.

3. The system of claim 1, further comprising one of: an EMG detector, EEG detector, an electromagnetic detector, an ultrasonic detector, an optical detector, a Hidden Markov Model (HMM) recognizer, a dynamic time warp (DTW) recognizer, a neural network, a fuzzy logic engine, or a Bayesian network.

4. The system of claim 1, further comprising a non-transitory computer medium configured to detect patient physical activity patterns and recognize body motion patterns for falls.

5. The system of claim 1, further comprising an in-door positioning system coupled to one or more mesh network appliances to provide location information.

6. The system of claim 1, further comprising a call center coupled to the analyzer to provide a human response.

7. The system of claim 1, wherein the 802 protocol comprises one of: an 802.11_protocol, an 802.15 protocol, an 802.16 protocol, a WiFi protocol, or a WIMAX® (Worldwide Interoperability for Microwave Access) protocol.

8. The system of claim 1, further comprising a wireless router and wherein the wireless router comprises one of: an 802.11 router, an 802.16 router, a WiFi router, a WiMAX® router, a Bluetooth® router, or an X10 router.

9. The system of claim 1, further comprising a mesh network appliance coupled to a power line to communicate X10 data to and from a mesh network.

10. The system of claim 1, further comprising a non-transitory computer medium configured to cause the IEEE 802 transmitter to transmit voice.

11. The system of claim 1, further comprising wireless sensors configured to be positioned on the person that allow a reflected signal to be isolated from radar clutter, and that sense additional body data not derived from the operational Doppler radar signal.

12. The system of claim 1, further comprising a security alarm coupled to the Doppler radar.

13. The system of claim 1, further comprising a non-transitory computer medium to reconstruct an image of a moving object on an opposite side of a wall from the analyzer.

14. The system of claim 1, wherein the analyzer is configured to track arm and leg movements to determine muscle weakness reflective of a health problem.

15. A monitoring system for a person, comprising:
a wireless local area network (WLAN) transceiver operating as a Doppler radar to wirelessly detect body movement of the person as part of a multiple input, multiple output (MIMO) wireless adapter, wherein the WLAN transceiver is configured to generate an operational Doppler radar signal; and a processor coupled to the WLAN transceiver to monitor body position, wherein the processor calibrates a training Doppler radar signal with a training body position during a training phase to develop a model and wherein the processor is configured to use the model with the operational Doppler radar signal during an operational phase to estimate body position of the person.

16. The system of claim 15, wherein the processor is configured to detect body movements due to breathing or to heart movement.

17. The system of claim 15, wherein the processor is configured to identify one person from another using each person's rib cage signature.

18. The system of claim 15, wherein the processor is configured to monitor the person for physical activity patterns and recognize body motion patterns leading to falls.

* * * * *